United States Patent
Guo et al.

(10) Patent No.: US 12,187,800 B2
(45) Date of Patent: Jan. 7, 2025

(54) ANTI-B7-H3 ANTIBODY

(71) Applicants: SUZHOU KANOVA BIOPHARMACEUTICAL CO., LTD., Jiangsu (CN); BEIJING KANOVA BIOPHARMACEUTICAL CO., LTD., Beijing (CN)

(72) Inventors: Li Guo, Beijing (CN); Yuan Dou, Beijing (CN); Tiantian Sun, Beijing (CN); Jiaming Li, Beijing (CN); Xiaoxu Qi, Beijing (CN); Chen Dong, Beijing (CN)

(73) Assignees: SUZHOU KANOVA BIOPHARMACEUTICAL CO., LTD., Jiangsu (CN); BEIJING KANOVA BIOPHARMACEUTICALS CO. LTD., Beijing (CN)

(*) Notice: Subject to any disclaimer, the term of this patent is extended or adjusted under 35 U.S.C. 154(b) by 890 days.

(21) Appl. No.: 17/295,896

(22) PCT Filed: Nov. 22, 2018

(86) PCT No.: PCT/CN2018/117011
§ 371 (c)(1),
(2) Date: May 21, 2021

(87) PCT Pub. No.: WO2020/103100
PCT Pub. Date: May 28, 2020

(65) Prior Publication Data
US 2022/0119529 A1  Apr. 21, 2022

(51) Int. Cl.
*C07K 16/28*  (2006.01)
*A61P 35/00* (2006.01)

(52) U.S. Cl.
CPC .......... *C07K 16/2827* (2013.01); *A61P 35/00* (2018.01); *C07K 2317/24* (2013.01); *C07K 2317/565* (2013.01); *C07K 2317/73* (2013.01); *C07K 2317/76* (2013.01); *C07K 2317/92* (2013.01)

(58) Field of Classification Search
CPC ............ C07K 16/2827; C07K 2317/24; C07K 2317/565; C07K 2317/73; C07K 2317/76; C07K 2317/92; C07K 2317/33; C07K 2317/56; A61P 35/00; A61K 2039/505; G01N 33/57492; G01N 33/574
See application file for complete search history.

(56) References Cited

U.S. PATENT DOCUMENTS

2018/0185510 A1  7/2018  Lerchen et al.

FOREIGN PATENT DOCUMENTS

| WO | WO-2016033225 A2 * | 3/2016 | ............ A61K 35/17 |
| WO | WO2016106004 A1 | 6/2016 | |
| WO | WO2017214335 A1 | 12/2017 | |

OTHER PUBLICATIONS

Deryk Loo et al., Development of an Fc-Enhanced Anti-B7-H3 Monoclonal Antibody with Potent Antitumor Activity, Clinical Cancer Research, vol. 18, No. 14, Jul. 15, 2012, pp. 3834-3845.

* cited by examiner

*Primary Examiner* — Nelson B Moseley, II
*Assistant Examiner* — Alyssa Rae Stonebraker
(74) *Attorney, Agent, or Firm* — Adam Warwick Bell; Matthew Rupert Kaser

(57) ABSTRACT

The present invention encompasses antibodies and fragments thereof that bind to an extracellular domain of B7H3, and uses thereof.

17 Claims, 6 Drawing Sheets

Figure 1A:
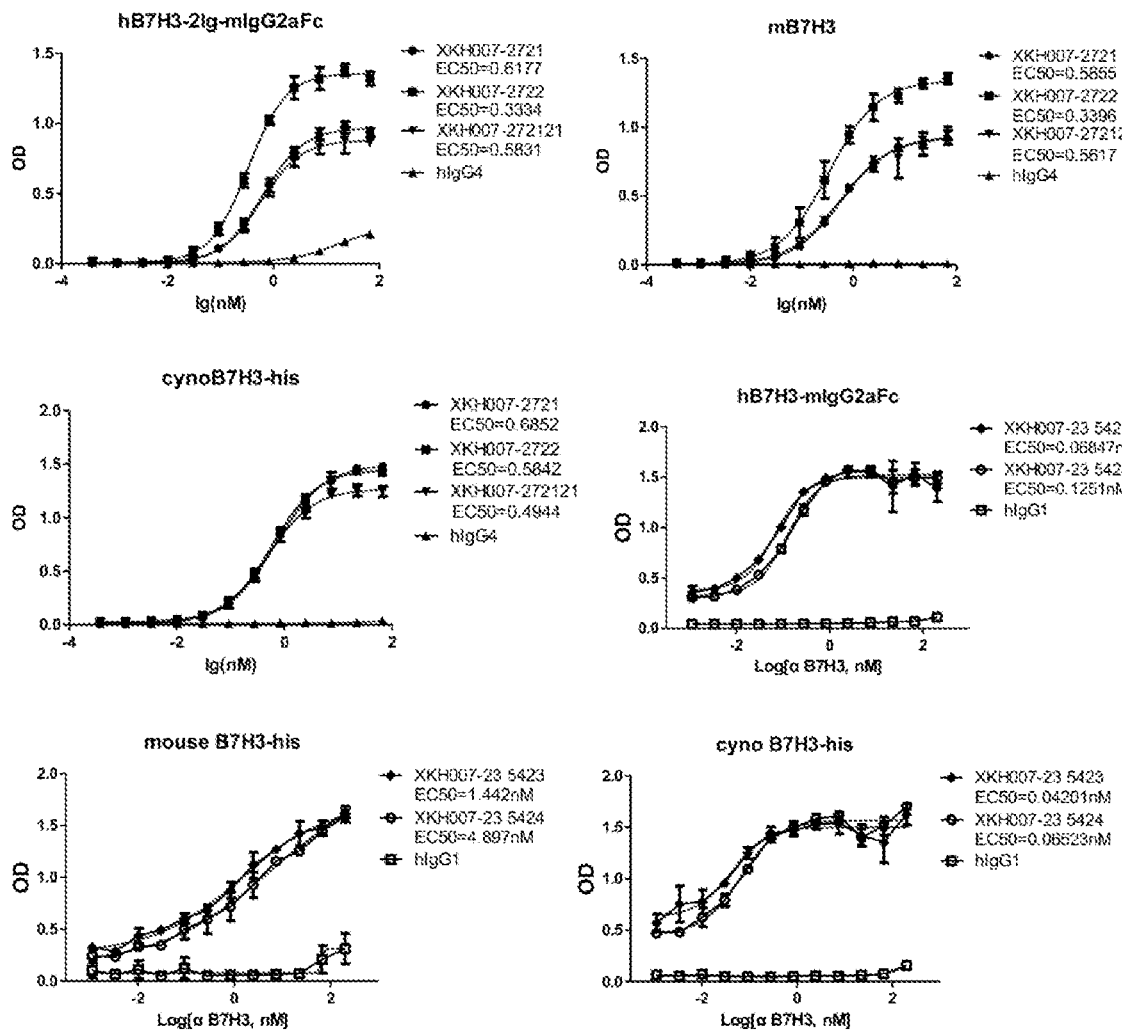

Specification includes a Sequence Listing.

ANTI-B7-H3 ANTIBODY

The present invention is related to antibodies and their immunoreactive fragments binding to an extracellular domain of B7H3 (B7-H3) molecule and the uses thereof, particularly in the treatment of cancers. The invention particularly concerns humanized anti-B7-H3 antibodies and their antigen binding fragments capable of enhancing the activation of the immune system against diseased tissues including cancerous cells.

SEQUENCE LISTING

A sequence listing text (.txt) file is submitted herewith under 37 CFR. 1.821 (c) and is hereby incorporated by reference in it's entirely. The details of the file as required under 37 CFR. 1.52(e)(5) and 37 CFR 1.77(b)(5) are as follows: Name of file is sequence-listing_ST25.txt; date of creation is 16 May 2021; size is 10,503 bytes. The content of the sequence listing information recorded in computer readable form is identical to the written sequence listing (if any) and identical to the sequence information provided with the original filed application and with the priority application, and contains no new matter. The information recorded in electronic form (if any) submitted (under Rule 13ter, if appropriate) with this application is identical to the sequence listing as contained in the application as filed.

BACKGROUND OF THE INVENTION

The B7 homology 3 protein (B7-H3) (also known as CD276 and B7RP-2, and referred to herein as "B7-H3" or "B7H3") is a type I transmembrane glycoprotein of the immunoglobulin superfamily Currently, there have been found seven members of the B7 superfamily: B7.1 (CD80), B7.2 (CD86), the inducible co-stimulator ligand (ICOS-L), the programmed death-1 ligand (PD-L1), the programmed death-2 ligand (PD-L2), B7-H3 and B7-H4 (Collins, M. et al. (2005) "The B7 Family of Immune-Regulatory Ligands," Genome Biol. 6:223.1-223.7).

Human B7-H3 contains a putative signal peptide, V-like and C-like Ig domains, a transmembrane region and a cytoplasmic domain. There are two isoforms of Human B7-H3, i.e., 2IgB7-H3 isoform having a single IgV-IgC-like domain (2IgB7-H3 isoform) and 4IgB7-H3 isoform having IgV-IgC-IgV-IgC-like domain. The predominant B7-H3 isoform in human tissues and cell lines is the 4IgB7-H3 isoform (Steinberger et al, J. Immunol. 172(4): 2352-9 (2004)).

B7-H3 is not constitutively expressed in many immune cells including natural killer (NK) cells, T-cells, and antigen-presenting cells (APCs), however, its expression is inducible, for example, by cytokines, such as IFN-γ and GM-CSF (Sharpe, A. H. et al. (2002) "The B7-CD28 Superfamily," Nature Rev. Immunol. 2:1 16-126). B7-H3 transcripts are also expressed in a variety of human tissues including colon, heart, liver, placenta, prostate, small intestine, testis, and uterus, as well as osteoblasts, fibroblasts, epithelial cells, and other cells of non-lymphoid lineage (Nygren et al. Front Biosci. 3:989-93 (2011)). However, protein expression in normal tissue is typically maintained at a low level.

B7-H3 is also expressed in a variety of human cancers, including prostate cancer, clear cell renal cell carcinoma, glioma, melanoma, lung cancer, non-small cell lung cancer (NSCLC), small cell lung cancer, pancreatic cancer, gastric cancer, acute myeloid leukemia (AML), non-Hodgkin's lymphoma (NHL), ovarian cancer, colorectal cancer, colon cancer, renal cancer, hepatocellular carcinoma, kidney cancer, head and neck cancer, hypopharyngeal squamous cell carcinoma, glioblastoma, neuroblastoma, breast cancer, endometrial cancer, and urothelial cell carcinoma.

Antibodies and other molecules that specifically bind to B7-H3 have been described (see, U.S. Pat. Nos. 7,527,969; 7,368,554; 7,358,354; and 7,279,567; PCT Publications Nos. WO 2008/116219; WO 2006/016276; WO 2004/093894; WO 04/001381; WO 2002/32375; WO 2002/10187 and WO 2001/094413, EP 1292619B). Despite all the antibodies and molecules, there remains a need for improved antibodies or molecules capable of binding to cancer cells and of facilitating or mediating an immune response against cancer cells, and thus can be used in diagnosing and treating such cancers.

SUMMARY OF THE INVENTION

Provided herein are an antibody and its immunoreactive fragments binding to B7H3 (B7-H3) molecule expressed on cells (for example, cancer cells) with high affinity and facilitating effective immune response against cancer cells. The antibody and its immunoreactive fragments provided herein are capable of enhancing the activation of the immune system, and thus provide important therapeutic and diagnostic agents for use in targeting pathological conditions associated with expression and/or activity of B7-H3 molecule. Accordingly, the invention provides methods, compositions, kits and articles of manufacture related to B7-H3 binding.

In one aspect, the present invention provides an isolated antibody or antigen binding fragment thereof, comprising a heavy chain (HC) variable region sequence and a light chain (LC) variable region sequence, wherein the antibody binds to an extracellular domain of B7-H3 with a binding affinity of about 1.5 nM or better than 1.5 nM, as determined by SPR analysis, for example, 1.0-1.4 nM, 0.5-1.0 nM, 0.1-0.5 nM, 0.4 nM, 0.3 nM, 0.2 nM, 0.1 nM, or better, as determined by SPR analysis.

In certain embodiments, the present invention provides an antibody or antigen binding fragment thereof of claim 1, wherein
(a) the HC comprises a CDR3 sequence comprising STALATDY (SEQ ID NO: 3) or STALATGY (SEQ ID NO: 9); or
(b) the LC comprises a CDR3 sequence comprising QQWSSYPLT (SEQ ID NO: 6) or QQWSSYPLT (SEQ ID NO: 12); or
(c) the HC comprises a CDR3 sequence comprising STALATDY (SEQ ID NO: 3) and the LC comprises a CDR3 sequence comprising QQWSSYPLT (SEQ ID NO: 6); or
(d) the HC comprises a CDR3 sequence comprising STALATGY (SEQ ID NO: 9) and the LC comprises a CDR3 sequence comprising QQWSSYPLT (SEQ ID NO: 12).

In certain embodiments, the HC further comprises a CDR2 sequence comprising MIHPNSGTFNYNERFKR (SEQ ID NO: 2) or MIHPNSGAFNYNERFKT (SEQ ID NO: 8). In certain embodiments, the HC further comprises a CDR1 sequence comprising GYNFNNYWMH (SEQ ID NO: 1) or GYTFTNYWMH (SEQ ID NO: 7). In certain embodiments, the HC further comprises a CDR1 sequence comprising GYNFNNYWMH (SEQ ID NO: 1) or GYTFTNYWMH (SEQ ID NO: 7). In certain embodiments, the LC further comprises a CDR2 sequence comprising DTSNLAS (SEQ ID NO: 5) or DTSNLAS (SEQ ID NO: 11). In certain embodiments, the LC further comprises a CDR1 sequence comprising SASSSVSYMY (SEQ ID NO: 4) or SASSSVSYMY(SEQ ID NO: 10). In certain embodiments, the HC comprises
- (a) a HC CDR1 comprising the amino acid sequence GYNFNNYWMH (SEQ ID NO: 1); and/or
- (b) a HC CDR2 comprising the amino acid sequence MIHPNSGTFNYNERFKR (SEQ ID NO: 2); and/or
- (c) a HC CDR3 comprising the amino acid sequence STALATDY (SEQ ID NO: 3); and/or the LC comprises
- (a) a LC CDR1 comprising the amino acid sequence SASSSVSYMY (SEQ ID NO: 4); and/or
- (b) a LC CDR2 comprising the amino acid sequence DTSNLAS (SEQ ID NO: 5); and/or
- (c) a LC CDR3 comprising the amino acid sequence QQWSSYPLT (SEQ ID NO: 6).

In certain embodiments, the HC comprises
- (a) a HC CDR1 comprising the amino acid sequence GYTFTNYWMH (SEQ ID NO: 7); and/or
- (b) a HC CDR2 comprising the amino acid sequence MIHPNSGAFNYNERFKT (SEQ ID NO: 8); and/or
- (c) a HC CDR3 comprising the amino acid sequence STALATGY (SEQ ID NO: 9); and/or the LC comprises
- (a) a LC CDR1 comprising the amino acid sequence SASSSVSYMY (SEQ ID NO: 10); and/or
- (b) a LC CDR2 comprising the amino acid sequence DTSNLAS (SEQ ID NO: 11); and/or
- (c) a LC CDR3 comprising the amino acid sequence QQWSSYPLT (SEQ ID NO:12).

In certain embodiments, the antibody is a chimeric antibody, humanized antibody, or human antibody. In certain embodiments, the antibody or antigen binding fragment thereof of the present invention further comprises a human acceptor framework. In certain embodiments, the human acceptor framework is derived from a human immunoglobulin framework or a human consensus framework. In certain embodiments, the human acceptor framework comprises subgroup kappa I framework sequences for VL, and subgroup III framework sequences for VH. Generally, the subgroup of sequences is a subgroup as in Kabat et al., Sequences of Proteins of Immunological Interest, Fifth Edition, NIH Publication 91-3242, Bethesda MD (1991), vols. 1-3. In certain embodiments, for the VL, the subgroup is subgroup kappa I as in Kabat et al, supra. In certain embodiments, for the VH, the subgroup is subgroup III as in Kabat et al, supra.

In certain embodiments, the antibody or antigen binding fragment thereof comprises human consensus framework. In some embodiments, the antibody or antigen binding fragment thereof comprises human consensus framework with amino acid sequence changes, for example, 1-15, 1-10, 2-9, 3-8, 4-7 or 5-6 amino acid changes.

In certain embodiments, the antibody or antigen binding fragment thereof of the invention comprises the HC variable region sequence comprising any amino acid sequence selected from the group consisting of SEQ ID NO: 13, SEQ ID NO: 16, SEQ ID NO: 17, and an amino acid sequence having more than 80%, 85%, 90%, 91%, 92%, 93%, 94%, 95%, 96%, 97%, 98% or 99% identity with any one of SEQ ID NOS: 13, 16 and 17. In certain embodiments, the antibody or antigen binding fragment thereof of the invention comprises the LC variable region sequence comprising any amino acid sequence selected from the group consisting of SEQ ID NO: 14, SEQ ID NO: 15, SEQ ID NO: 18, SEQ ID NO: 19, and an amino acid sequence having more than 80%, 85%, 90%, 91%, 92%, 93%, 94%, 95%, 96%, 97%, 98% or 99% identity with any one of SEQ ID NOS: 14, 15, 18 and 19. In certain embodiments, the HC variable region sequence comprises amino acid sequence of SEQ ID NO: 13 and the LC variable region sequence comprises amino acid sequence of SEQ ID NO: 14 or SEQ ID NO: 15. In certain embodiments, the HC variable region sequence comprises amino acid sequence of SEQ ID NO: 16 or SEQ ID NO: 17 and the LC variable region sequence comprises amino acid sequence of SEQ ID NO: 18 or SEQ ID NO: 19. In certain embodiments, the antibody is an IgG1, IgG2 or IgG4 isotype. In certain embodiments, the antigen binding fragment is selected from the group consisting of Fab, F(ab')2, Fab', scFv, and Fv. In certain embodiments, the antibody or antigen binding fragment thereof of the invention is a blocking antibody or an antagonist antibody which inhibits or reduces biological activity of the B7-H3 molecule it binds. Preferred the blocking antibodies or antagonist antibodies substantially or completely inhibit the biological activity of the B7-H3 molecule.

In one aspect, the present invention provides a bispecific molecule comprising the antibody or antigen binding fragment thereof of the present invention and a second antibody or antigen binding fragment thereof. In certain embodiments, the second antibody or antigen binding fragment thereof specifically binds to a tumor antigen expressed on the surface of a tumor cell, wherein the tumor antigen is selected from the group consisting of A33; ADAM-9; ALCAM; BAGE; beta-catenin; CA125; Carboxypeptidase M; CD103; CD19; CD20; CD22; CD23; CD25; CD27; CD28; CD36; CD40/CD154; CD45; CD46; CD5; CD56; CD79a/CD79b; CDK4; CEA; CTLA4; Cytokeratin 8; EGF-R; EphA2; ErbB1; ErbB3; ErbB4; GAGE-1; GAGE-2; GD2/GD3/GM2; HER-2/neu; human papillomavirus-E6; human papillomavirus-E7; JAM-3; KID3; KID31; KSA (17-1A); LUCA-2; MAGE-1; MAGE-3; MART; MUC-1; MUM-1; N-acetylglucosaminyltransferase; Oncostatin M; p15; PIPA; PSA; PSMA; ROR1; TNF-β receptor; TNF-α receptor; TNF-γ receptor; Transferrin Receptor; and VEGF receptor.

In one aspect, the present invention provides a polypeptide comprising the antibody or antigen binding fragment thereof of the present invention.

In one aspect, the present invention provides a polypeptide comprising the CH variable region and/or LC variable region of the antibody or antigen binding fragment thereof of the present invention.

In one aspect, the present invention provides an immunoconjugate comprising the antibody or antigen binding fragment thereof of the present invention, linked to a therapeutic agent. In certain embodiments, the therapeutic agent is a cytotoxin or a radioactive isotope.

In one aspect, the present invention provides a composition comprising the antibody or antigen binding fragment thereof, the bispecific molecule, the polypeptide, the immunoconjugate of the present invention, and a pharmaceutically acceptable carrier. In certain embodiments, the composition further comprises an anti-cancer agent. In certain embodiments, the agent is an antibody, a chemotherapeutic agent, a radiation therapeutic agent, a hormonal therapeutic agent, a toxin or an immunotherapeutic agent.

In one aspect, the present invention provides an article of manufacture or kit for treating cancer, comprising the antibody or antigen binding fragment thereof, the bispecific molecule, the polypeptide, the immunoconjugate or the composition of the present invention, and package insert with necessary information about the use of the antibody or antigen binding fragment thereof, the bispecific molecule, the polypeptide, the immunoconjugate or the composition of the present invention.

In one aspect, the present invention provides an article of manufacture or kit for diagnosing cancer, comprising the antibody or antigen binding fragment thereof of the present invention, and package insert with necessary information about the use of the antibody or antigen binding fragment thereof of the present invention.

In one aspect, the present invention provides an isolated nucleic acid encoding the CH variable region and/or LC variable region of the antibody or antigen binding fragment thereof of the present invention, an expression vector comprising the nucleic acid, or a host cell comprising the expression vector.

In one aspect, the present invention provides a method for preparing an antibody or antigen binding fragment thereof comprising expressing the antibody or antigen binding fragment thereof in the host cell stated above and isolating the antibody or antigen binding fragment thereof from the host cell.

In one aspect, the present invention provides a method for treatment of a cancer, comprising administrating an effective amount of the antibody or antigen binding fragment thereof, the bispecific molecule, the polypeptide, the immunoconjugate, the composition, the article of manufacture or kit of the present invention, described above, to a subject having the cancer disease. In certain embodiments, the cancer is selected from the group consisting of: melanoma, colorectal adenocarcinoma, prostate cancer, breast cancer, colon cancer, lung cancer, gastric cancer, and renal clear cell carcinoma.

In one aspect, the present invention provides a method for detection or quantitation of expression or activity of B7-H3 polypeptide, comprising contacting the antibody or antigen binding fragment thereof of the present invention with a sample from a subject. In certain embodiments, the antibody or antigen binding fragment thereof is labeled with detectable substance. In certain embodiments, the antibody or antigen binding fragment thereof is radio-labeled, fluorescence-labeled or enzyme-labeled.

In one aspect, the present invention provides a method for predicting the risk of developing a cancer of a subject comprising detecting, quantitating, or monitoring expression or activity of B7-H3 polypeptide by using the antibody or antigen binding fragment thereof of the present invention.

In one aspect, the present invention provides a method for monitoring the effectiveness of an agent to treat a cancer exhibiting elevated expression or activity of B7-H3, comprising detection or quantitation of expression or activity of B7-H3 polypeptide by using the antibody or antigen binding fragment thereof of the present invention.

DRAWINGS

Figure 1B:
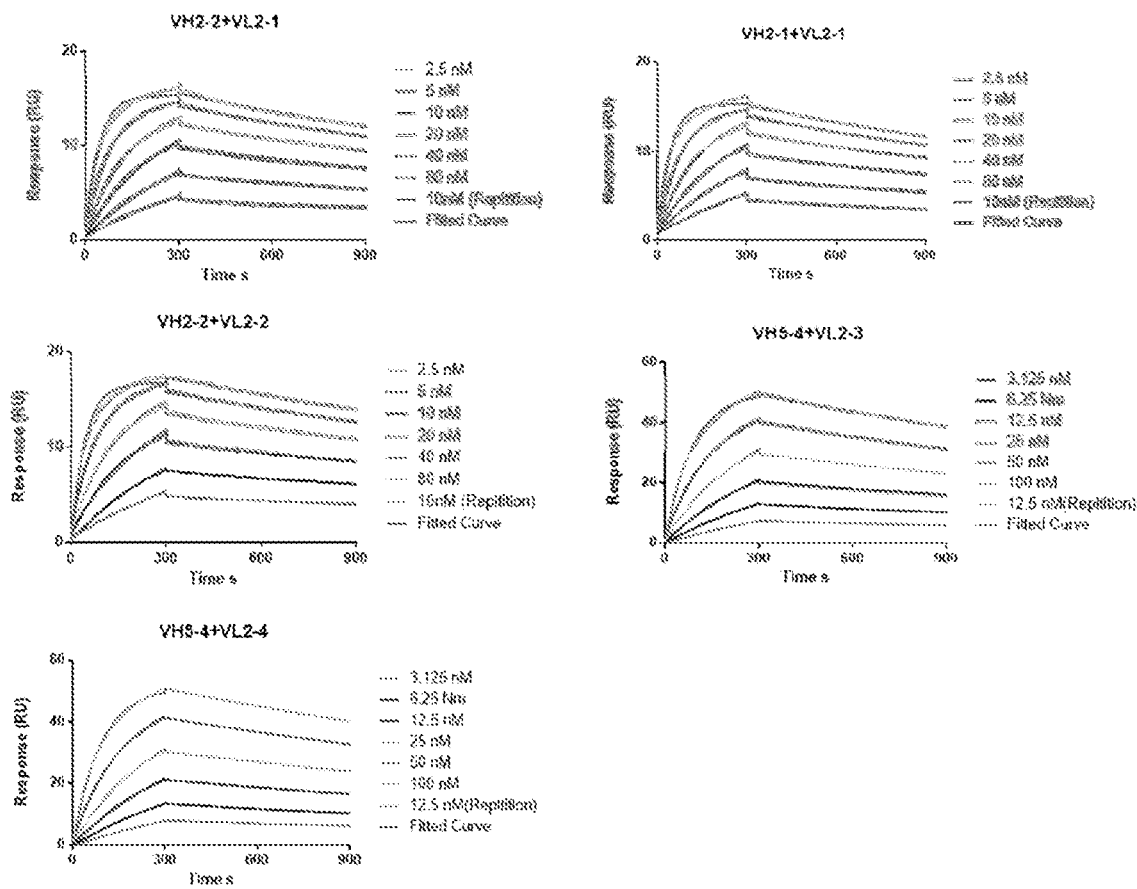

FIG. 1A-B. FIG. 1A shows experimental results of ELISA analysis of humanized anti-B7H3 antibodies of the present invention binding to human B7H3, mouse B7H3, and cynomolgus monkey B7H3 protein. FIG. 1B shows experimental results of Surface Plasmon Resonance (SPR) binding analysis using Biacore 8K. The data of dissociation (kd) and association (ka) rate constants were obtained using Biacore 8K evaluation software. The equilibrium dissociation constants (KD) were calculated from the ratio of kd over ka.

Figure 2:
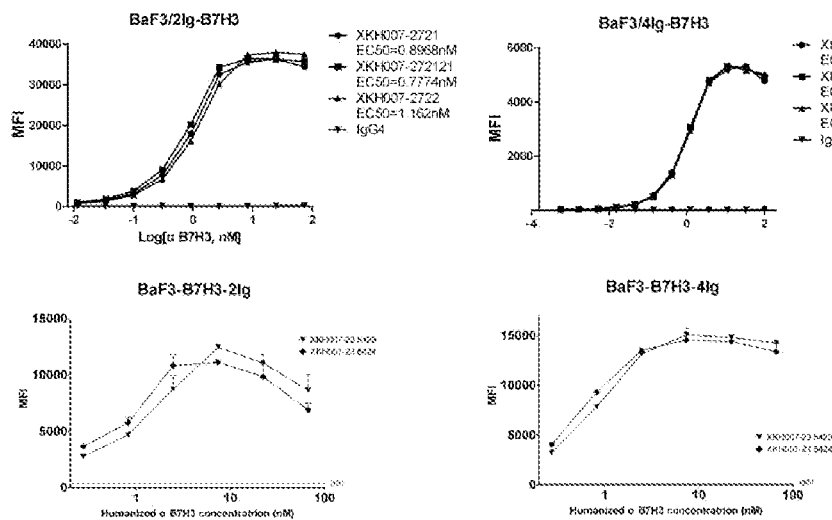

FIG. 2 Cell surface binding affinity of humanized anti-B7H3 antibodies with BaF3/B7H3-2Ig and BaF3/B7H3-4Ig stably expressed on the surface of cell lines.

Figure 3:
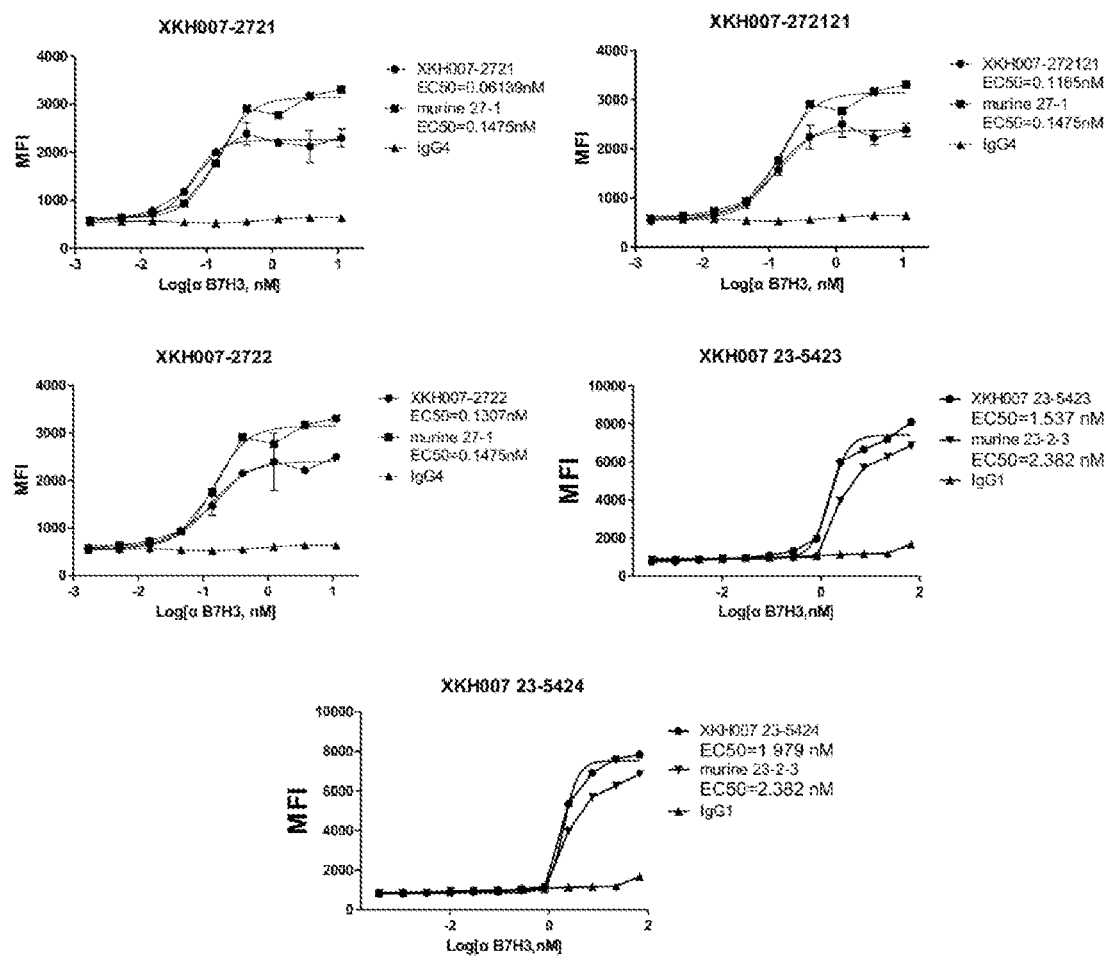

FIG. 3 Humanized anti-B7H3 antibodies binding affinity with B7H3 expressed on stimulated human PBMCs.

Figure 4:
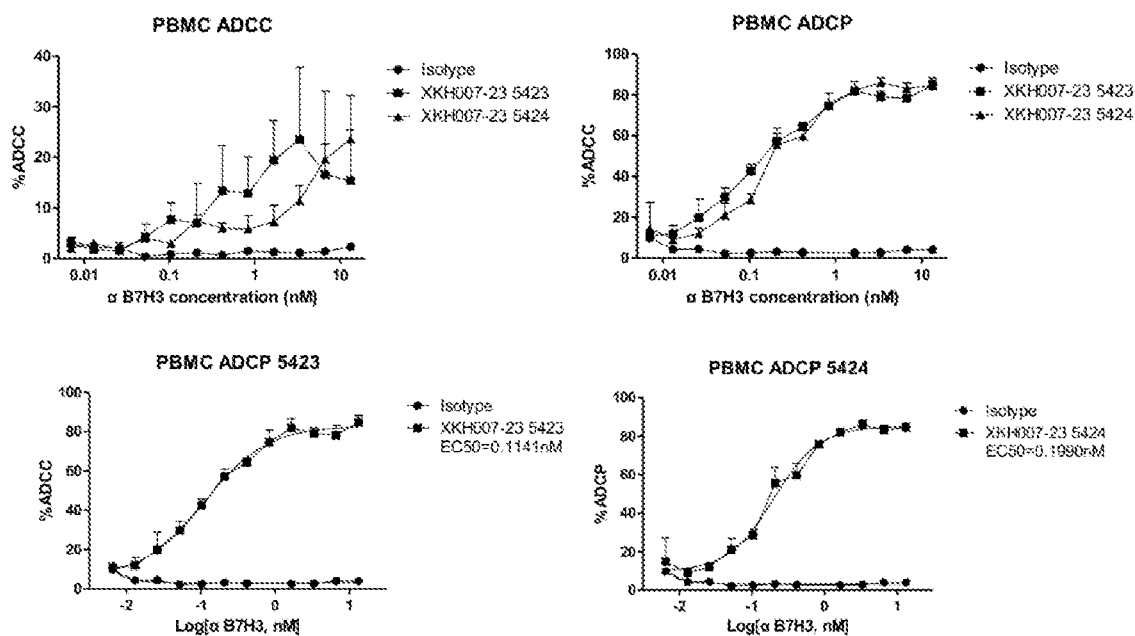

FIG. 4 Humanized anti-B7H3 antibody induced ADCC in vitro. The results show humanized anti-B7H3 antibodies are able to mediate ADCC as well as ADCP in a dose dependent manner.

Figure 5:
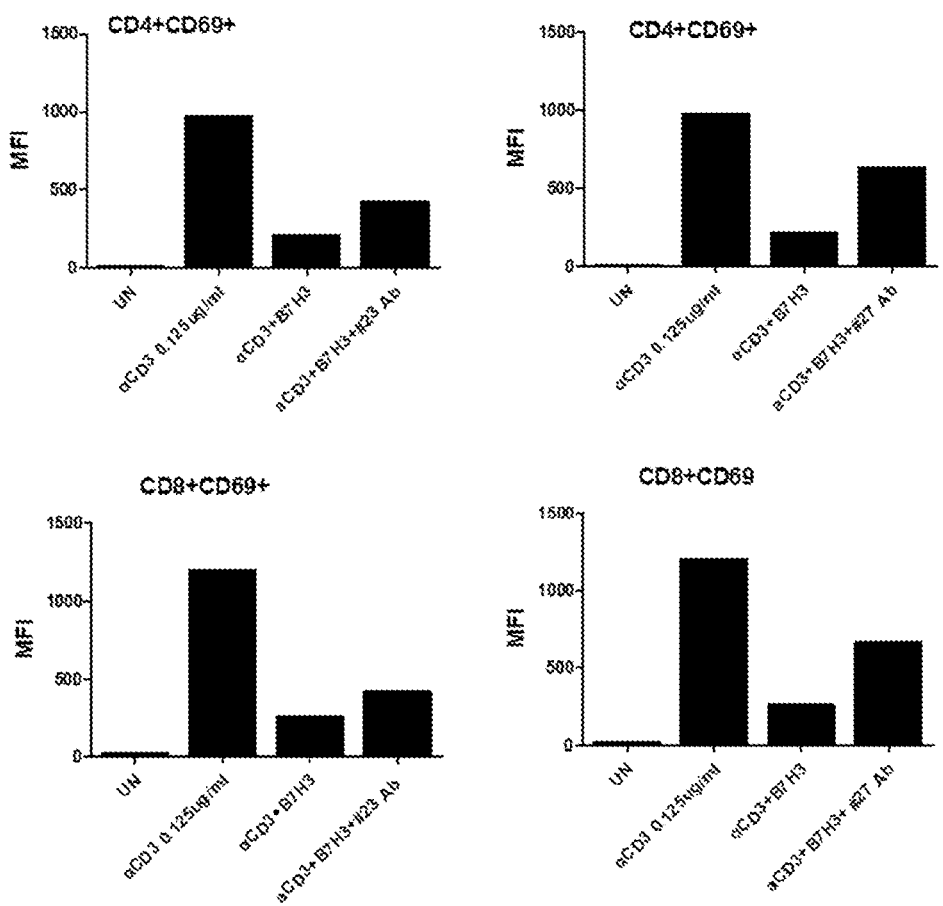

FIG. 5 Anti-B7H3 antibody blocked B7H3 inhibition of T cell activation. The results show anti-B7H3 Abs reverse the inhibition effect of B7H3 on anti-CD3 stimulated T cell activation.

Figure 6:
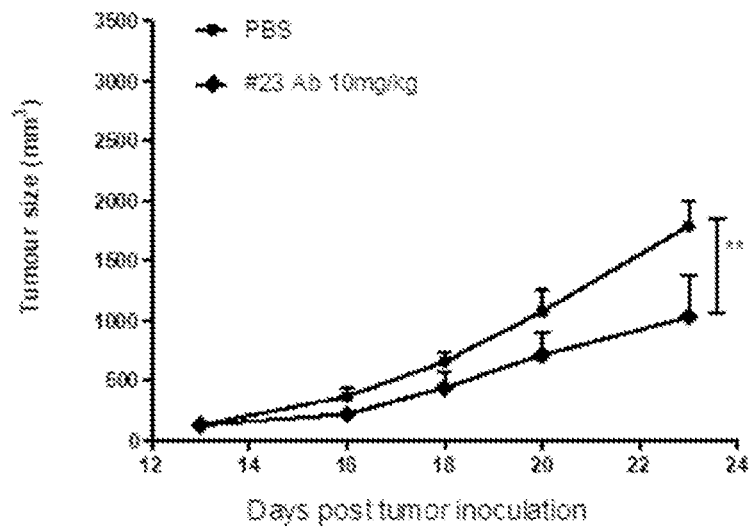

FIG. 6 B16F10 Murine Melanoma Syngeneic Model in C57BL6/J Mice. The results show the anti-B7H3 antibody can reduce melanoma tumor growth in in vivo studies.

Figure 7:
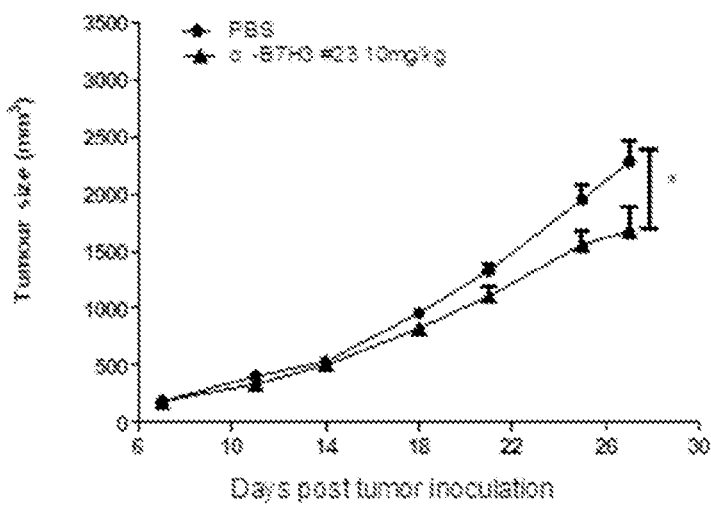

FIG. 7 SW620 Human Colorectal Adenocarcinoma Xenograft Model in BALB/C nude Mice. The results show the anti-B7H3 antibody can reduce human colorectal adenocarcinoma growth in xenograft model.

DETAILED DESCRIPTION OF THE INVENTION

The present invention herein provides antibodies and fragments thereof binding to B7-H3 protein, especially human B7-H3 protein or polypeptide. The present invention is also related to the use of the antibodies and fragments thereof for enhancing the activation of the immune system against for example cancer cells.

The invention further provides methods of making anti-B7-H3 antibodies, polynucleotides encoding anti-B7-H3 antibodies, and cells comprising polynucleotides encoding anti-B7-H3 antibodies.

1. Definition

It is to be understood that the present disclosure is not limited to the aspects described herein, as such may, of course, vary. It is also to be understood that the terminology used herein is for describing particular aspects only, and is not intended to be limiting, since the scope of the present disclosure will be limited only by the appended claims.

Unless defined otherwise, all technical and scientific terms used herein have the same meanings as commonly understood by one of ordinary skill in the art to which this technology belongs. All technical and patent publications cited herein are incorporated herein by reference in their entirety. Those skilled in the art will employ, unless otherwise indicated, conventional techniques of tissue culture, immunology, molecular biology, microbiology, cell biology and recombinant DNA, which are within the skill of the art. See, e.g., Sambrook and Russell eds. (2001) Molecular Cloning: A Laboratory Manual, 3rd edition; Harlow and Lane eds. (1999) Antibodies, A Laboratory Manual. MONOCLONAL ANTIBODIES: A PRACTICAL APPROACH (Shepherd, P. et al. Eds., 2000) Oxford University Press, USA, New York N.Y.

As used herein, "B7-H3" is a member of the B7/CD28 superfamily of costimulatory molecules serving as an accessory modulator of T-cell response. B7-H3 is a type I transmembrane protein that shares 20%-27% amino acid identity with other B7 family members. While murine B7-H3 consists of a single extracellular variable-type immunoglobulin (Ig)V-IgC domain and a signature intracellular domain (2Ig B7-H3), human B7-H3 possesses an additional isoform, the so-called 4Ig B7-H3 that contains a nearly exact tandem duplication of the IgV-IgC domain. B7H3 (2Ig) can be referred to: NCBI Reference Sequence: NM_025240.2; and B7H3(4Ig) can be referred to: NCBI Reference Sequence: NM_001024736.1. (Entrez Gene ID: 80381, UniProtKB: Q5ZPR3).

As used in the present invention, the term "antibody", also called "immunoglobulin", covers antibodies with structural characteristics of a native antibody and antibody-like molecules having structural characteristics different from a native antibody but exhibiting binding specificity to B7H3 molecule (B7-H3, CD276 and B7RP-2). The term antibody is intended to encompass immunoglobulin molecules and immunologically active fragments of immunoglobulin molecules, i.e., molecules that contain an antigen binding site. Immunoglobulin molecules can be of any type (e.g., IgG, IgE, IgM, IgD, IgA and IgY), class (e.g., IgG1, IgG2, IgG3, IgG4, IgA1 and IgA2) or subclass.

The terms "heavy chain" ("CH"), "light chain" ("CL"), "light chain variable region" ("VL"), "heavy chain variable region" ("VH"), "framework region" ("FR"), refer to domains in naturally occurring immunoglobulins and the corresponding domains of synthetic (e.g., recombinant) binding proteins (e.g., humanized antibodies). The basic structural unit of naturally occurring immunoglobulins (e.g., IgG) is a tetramer having two light chains and two heavy chains. The amino-terminal ("N") portion of each chain includes a variable region of about 100 to 110 or more amino acids primarily responsible for antigen recognition. The carboxy-terminal ("C") portion of each chain defines a constant region, with light chains having a single constant domain and heavy chains usually having three constant domains and a hinge region. Thus, the structure of the light chains of a naturally occurring IgG molecule is N-VL-CL-C and the structure of IgG heavy chains is N—VH-CH1-H-CH2-CH3-C (where H is the hinge region).

The variable region of an IgG molecule consists of the complementarity determining regions (CDRs), which contain the residues in contact with antigen and non-CDR segments, referred to as framework segments, which maintain the structure and determine the positioning of the CDR loops. Thus, the VL and VH domains have the structure N-FR1-CDR1-FR2-CDR2-FR3-CDR3-FR4-C.

In a native antibody, the variability is not evenly distributed through the variable regions of antibodies. It is concentrated in three segments called complementarity determining regions (CDRs) or hypervariable regions both in the light chain and the heavy chain variable regions. The more highly conserved portions of variable domains are called the framework (FR). The variable regions of native heavy and light chains each comprise four FR regions, connected by three CDRs. The CDRs in each chain are held together in proximity with the FR regions and, with the CDRs from the other chain, contribute to the formation of the antigen binding site of antibodies [see Kabat, E. A. et al., Sequences of Proteins of Immunological Interest National Institute of Health, Bethesda, MD (1987)]. The constant regions are not involved directly in binding an antibody to an antigen, but exhibit various effector functions, such as participation of the antibody in antibody-dependent cellular toxicity (ADCC).

The term of "antigen binding fragment" of an antibody (or simply "antibody fragment"), as used herein, refers to one or more fragments of an antibody that retain the ability to specifically bind to an antigen (e.g., B7H3 molecule (B7-H3, CD276 and B7RP-2), such as human B7H3). The antibody fragments comprise only a portion of an intact antibody, wherein the portion preferably retains at least one, preferably most or all, of the functions normally associated with that portion when present in an intact antibody. Examples of antibody fragments include Fab, Fab', F(ab')2, and Fv fragments; diabodies; linear antibodies; single-chain antibody molecules; and multispecific antibodies formed from antibody fragments.

Papain digestion of antibodies produces two identical antigen binding fragments, called "Fab" fragments, each with a single antigen binding site, and a residual Fc fragment, whose name reflects its ability to crystallize readily. The "Fab" fragment also contains the constant domain of the light chain and the first constant domain (CH1) of the heavy chain. "Fab" fragments differ from Fab fragments by the addition of a few residues at the carboxyl terminus of the heavy chain CH1 domain including one or more cysteines from the antibody hinge region. "Fab'-SH" is the designation for Fab' in which the cysteine residue(s) of the constant domains have a free thiol group. "F(ab')" fragments are produced by cleavage of the disulfide bond at the hinge cysteines of the "F(ab')2" which is pepsin digestion product.

"Fd" fragment consists of the VH and CH1 domains. A "dAb" fragment (Ward et al., (1989) Nature 341:544-546) consists of a VH domain. An isolated complementarity determining region (CDR) and a combination of two or more isolated CDRs which may optionally be joined by a synthetic linker.

A "Fv" fragment consists of the VL and VH domains of a single arm of an antibody. A single chain Fv (scFv) consists of one heavy- and one light-chain variable region covalently linked by a flexible peptide linker in one single polypeptide chain.

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA, 90:6444-48 (1993).

These antibody fragments are obtained using conventional techniques known to those with skill in the art, for example, by recombinant DNA techniques, or by enzymatic or chemical cleavage of intact immunoglobulins.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising in the monoclonal antibody preparation, such variants generally being present in minor amounts.

As used herein, the term "chimeric antibody" means an antibody in which the Fc constant region of a monoclonal antibody from one species (e.g., a mouse Fc constant region) is replaced, using recombinant DNA techniques, with an Fc constant region from an antibody of another species (e.g., a human Fc constant region). See for example, Robinson et al., PCT/US86/02269; Morrison et al., European Patent Application 173,494.

As used herein, the term "humanized antibody" refers to an antibody including a human framework region and one or more CDRs from a non-human (for example a mouse, rat, rabbit or synthetic) immunoglobulin. The non-human immunoglobulin providing the CDRs is termed a "donor," and the human immunoglobulin providing the framework is termed an "acceptor." In one aspect, all the CDRs are from the donor immunoglobulin in a humanized immunoglobulin. Hence, all parts of a humanized immunoglobulin, except possibly the CDRs, are substantially identical to corresponding parts of natural human immunoglobulin sequences. Humanized antibodies can be constructed by means of genetic engineering (see for example, U.S. Pat. No. 5,585,089).

An "acceptor human framework" means a framework comprising the amino acid sequence of a light chain variable domain (VL) framework or a heavy chain variable domain (VH) framework derived from a human immunoglobulin framework or a human consensus framework. An acceptor human framework "derived from" a human immunoglobulin framework or a human consensus framework may comprise the same amino acid sequence thereof, or it may contain amino acid sequence changes. In some embodiments, the number of amino acid changes is 1-10, 2-9, 3-8, 4-7 or 5-6.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., Sequences of Proteins of Immunological Interest, Fifth Edition, NIH Publication 91-3242, Bethesda MD (1991), vols. 1-3. In certain embodiments, for the VL, the subgroup is subgroup kappa I as in Kabat et al, supra. In certain embodiments, for the VH, the subgroup is subgroup III as in Kabat et al, supra.

The term "human antibody" as used herein, is intended to include antibodies having variable and constant regions derived from human germline immunoglobulin sequences. The human antibodies of the present technology may include amino acid residues not encoded by human germline immunoglobulin sequences (e.g., mutations introduced by random or site-specific mutagenesis in vitro or by somatic mutation in vivo). However, the term "human antibody" as used herein, is not intended to include antibodies in which CDR sequences derived from the germline of another mammalian species, such as a rabbit, have been grafted onto human framework sequences. Thus, as used herein, the term "human antibody" refers to an antibody in which substantially every part of the protein (e.g., CDR, framework, CL, CH domains (e.g., CH1, CH2, CH3), hinge, VL, VH) is substantially non-immunogenic in humans, with only minor sequence changes or variations. Thus, a human antibody is distinct from a chimeric or humanized antibody. It is pointed out that a human antibody can be produced by a non-human animal or prokaryotic or eukaryotic cell that is capable of expressing functionally rearranged human immunoglobulin (e.g., heavy chain and/or light chain) genes.

As used herein the phrase "bispecific antibody" or "bispecific antigen binding antibody" or "bifunctional antibody" is an artificial hybrid antibody having two different heavy/light chain pairs and two different binding sites. As far as the present invention is concerned, the "bispecific antibody" specifically binds to B7H3 and another antigen, for example, a tumor antigen expressed on a tumor cell.

A "conjugate" is an antibody conjugated to one or more heterologous molecule(s), including but not limited to a cytotoxic agent.

A "blocking" antibody or an "antagonist" antibody is one which inhibits or reduces biological activity of the antigen it binds. Preferred blocking antibodies or antagonist antibodies substantially or completely inhibit the biological activity of the antigen.

The term "isolated" as used herein refers to molecules or biological or cellular materials being substantially free from other materials. For example, a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides.

As used herein, percent of "homology" or "identity" is used in the context of two or more nucleic acids or polypeptide sequences, referring to two or more sequences or subsequences that are the same or have a specified percentage of nucleotides or amino acid residues that are the same, e.g., at least 80% identity, preferably at least 85%, 90%, 91%, 92%, 93%, 94%, 95%, 96%, 97%, 98%, 99%, or higher identity over a specified region (e.g., nucleotide sequence encoding an antibody described herein or amino acid sequence of an antibody described herein). Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. The alignment and the percent homology or sequence identity can be determined using software programs known in the art. Preferably, default parameters are used for alignment. A preferred alignment program is BLAST, using default parameters. Preferred programs are BLASTN and BLASTP. Details of these programs can be found at the following Internet address: ncbi.nlm.nih.gov/cgi-bin/BLAST.

"Affinity" refers to the total strength of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). Affinity can be measured by common methods known in the art, including, for example, Biacore, radioimmunoassay (RIA) and ELISA.

The affinity of a molecule X for its partner Y can generally be represented by equilibrium dissociation constant (KD), calculated as the ratio $k_{off}/k_{on}(k_d/k_a)$. See, e.g., Chen, Y., et al., (1999) J. Mol Biol 293:865-881. Low-affinity antibodies generally bind antigen slowly and tend to dissociate readily, whereas high-affinity antibodies generally bind antigen faster and tend to remain bound longer. In one embodiment of the invention, the "dissociation rate $(k_d)$" is measured by using surface plasmon resonance assays. An "on-rate" or "rate of association" or "association rate $(k_a)$" or "$k_{on}$" according to this invention can also be determined with the same surface plasmon resonance technique and calculated using a simple one-to-one Langmuir binding model (BIAcore Evaluation Software) by simultaneous fitting the association and dissociation sensorgram.

The term "EC50", as used herein, refers to the concentration of an antibody or an antigen-binding fragment thereof, which binds to B7H3 and/or induces a response, either in an in vitro or an in vivo assay, which is 50% of the maximal binding or response, i.e., halfway between the maximal binding or response and the baseline.

The terms "cancer," "neoplasm," and "tumor," can be used interchangeably in the present invention, referring to a neoplasm or tumor resulting from abnormal uncontrolled growth of cells that makes them pathological to the host organism. In some embodiments, cancer refers to a benign tumor, which has remained localized. In other embodiments, cancer refers to a malignant tumor, which has invaded and destroyed neighboring body structures and spread to distant sites. In some embodiments, the cancer is associated with a specific cancer antigen.

As used herein, "treating" or "treatment" of a disease in a subject refers to an approach for obtaining beneficial or desired results, including one or more, but are not limited to, alleviation or amelioration of one or more symptoms, diminishment of extent of a condition (including a disease), stabilized (i.e., not worsening) state of a condition (including disease), delay or slowing of condition (including disease), progression, amelioration or palliation of the condition (including disease), states and remission (whether partial or total), whether detectable or undetectable.

A "pharmaceutically acceptable carrier" is a carrier with which an active ingredient constitutes a pharmaceutical formulation. A pharmaceutically acceptable carrier includes, but is not limited to, a buffer, excipient, stabilizer, or preservative.

The term "package insert" is used to refer to instructions customarily included in commercial package of a therapeutic product. Generally, there is information about the use of the therapeutic product on the package insert such as indications, usage, dosage, administration, combination therapy, contraindications and/or warnings.

The present invention will be described with respect to particular embodiments and with reference to certain drawings, but the invention is not limited thereto but only by the claims. The term "comprising" as used in the present description and claims does not exclude other elements or steps. Where an indefinite or definite article is used when referring to a singular noun e.g. "a" or "an", "the", this includes a plural of that noun unless something else is specifically stated.

2. Anti-B7-H3 Antibody and Methods of Preparing the Same

This invention encompasses isolated anti-B7-H3 antibodies or fragments thereof, polynucleotides comprising sequences encoding the anti-B7-H3 antibodies or fragments thereof.

The anti-B7-H3 antibodies of the invention are preferably monoclonal. Also encompassed within the scope of the invention are Fab, Fab', Fab'-SH and F(ab')2 fragments of the anti-B7-H3 antibodies provided herein. These antibody fragments can be created by traditional means, such as enzymatic digestion, or may be generated by recombinant techniques. The anti-B7-H3 antibodies and fragments thereof are useful for the diagnostic and therapeutic purposes, including diagnosis and therapy of cancers.

Monoclonal antibodies are obtained from a population of substantially homogeneous antibodies, i.e., the individual antibodies comprising the population are identical except for possible naturally occurring mutations that may be present in minor amounts. Thus, the modifier "monoclonal" indicates the character of the antibody as not being a mixture of different antibodies. The monoclonal anti-B7-H3 antibodies of the invention can be made using the hybridoma method or recombinant DNA methods (U.S. Pat. No. 4,816,567).

In the hybridoma method, a mouse or other appropriate host animal, such as a hamster, is immunized by a whole B7-H3 molecule or part of the molecule, for example, a polypeptide comprising the extracellular domain of B7-H3, together with an adjuvant. A B7-H3 molecule or a polypeptide comprising the extracellular domain of A B7-H3 molecule may be prepared using methods well-known in the art. In one embodiment, animals are immunized with a polypeptide that contains the extracellular domain (ECD) of B7-H3 fused to the Fc portion of an immunoglobulin heavy chain. In one embodiment, animals are immunized with an B7-H3-IgG1 fusion protein. Two weeks later the animals are boosted. 7 to 14 days later, animals are bled and the serum is assayed for anti-B7-H3 titer. Animals are boosted until titer plateaus. Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, pp. 59-103 (Academic Press, 1986)).

The hybridoma cells thus prepared are seeded and grown in a suitable culture medium that preferably contains one or more substances that inhibit the growth or survival of the unfused, parental myeloma cells. Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as SP-2 or X63-Ag8-653 cells. Human myeloma and mouse-human heteromyeloma cell lines also have been described for the production of human monoclonal antibodies (Kozbor, J. Immunol, 133:3001 (1984); Brodeur et al, Monoclonal Antibody Production Techniques and Applications, pp. 51-63 (Marcel Dekker, Inc., New York, 1987)).

Culture medium in which hybridoma cells are growing is assayed for production of monoclonal antibodies directed against B7-H3. Preferably, the binding specificity of monoclonal antibodies produced by hybridoma cells is determined by immunoprecipitation or by an in vitro binding assay, such as radioimmunoassay (RIA) or enzyme-linked immunoadsorbent assay (ELISA).

The binding affinity of the monoclonal antibody can then be determined by conventional methods in the art. After hybridoma cells are identified that produce antibodies of the desired specificity, affinity, and/or activity, the clones may be subcloned by limiting dilution procedures and grown by standard methods (Goding, Monoclonal Antibodies: Principles and Practice, pp. 59-103 (Academic Press, 1986)).

Suitable culture media for this purpose include, for example, D-MEM or RPMI-1640 medium. In addition, the hybridoma cells may be grown in vivo as ascites tumors in an animal. The monoclonal antibodies secreted by the subclones are suitably separated from the culture medium, ascites fluid, or serum by conventional immunoglobulin purification procedures.

The anti-B7-H3 antibodies of the invention can be made by using combinatorial libraries to screen for synthetic antibody clones with the desired activity or activities. In principle, synthetic antibody clones are selected by screening phage libraries containing phage that display various fragments of antibody variable region (Fv) fused to phage coat protein. Such phage libraries are panned by affinity chromatography against the desired antigen.

Clones expressing Fv fragments capable of binding to the desired antigen are adsorbed to the antigen and thus separated from the non-binding clones in the library. The binding clones are then eluted from the antigen, and can be further enriched by additional cycles of antigen adsorption/elution. Any of the anti-B7-H3 antibodies of the invention can be obtained by designing a suitable antigen screening procedure to select for the phage clone of interest followed by construction of a full length anti-B7-H3 antibody clone using the Fv sequences from the phage clone of interest and suitable constant region (Fc) sequences described in Kabat et al, Sequences of Proteins of Immunological Interest, Fifth Edition, NIH Publication 91-3242, Bethesda MD (1991), vols. 1-3.

Repertoires of VH and VL genes can be separately cloned by polymerase chain reaction (PCR) and recombined randomly in phage libraries, which can then be searched for antigen-binding clones as described in Winter et al, Ann. Rev. Immunol, 12: 433-455 (1994). Libraries from immunized sources provide high-affinity antibodies to the immunogen without the requirement of constructing hybridomas. Alternatively, the naive repertoire can be cloned to provide a single source of human antibodies to a wide range of non-self and also self antigens without any immunization as described by Griffiths et al, EMBO J, 12: 725-734 (1993). Finally, naive libraries can also be made synthetically by cloning the unrearranged V-gene segments from stem cells, and using PCR primers containing random sequence to encode the highly variable CDR3 regions and to accomplish rearrangement in vitro as described by Hoogenboom and Winter, J. MoI Biol, 227: 381-388 (1992).

The antibodies produced by naive libraries (either natural or synthetic) can be of moderate affinity, but affinity maturation can also be mimicked in vitro by constructing and reselecting from secondary libraries. For example, mutation can be introduced at random in vitro by using error-prone polymerase (reported in Leung et al., Technique, 1: 11-15 (1989)) in the method of Hawkins et al., J. MoL Biol., 226: 889-896 (1992) or in the method of Gram et al., Proc. Natl. Acad. Sci USA, 89: 3576-3580 (1992). Additionally, affinity maturation can be performed by randomly mutating one or more CDRs, e.g. using PCR with primers carrying random sequence spanning the CDR of interest, in selected individual Fv clones and screening for higher affinity clones. Another effective approach is to recombine the VH or VL domains selected by phage display with repertoires of naturally occurring V domain variants obtained from unimmunized donors and screen for higher affinity in several rounds of chain reshuffling as described in Marks et al., BiotechnoL, 10: 779-783 (1992).

It is possible to select between phage antibodies of different affinities, even with affinities that differ slightly, for B7-H3. However, random mutation of a selected antibody (e.g. as performed in some of the affinity maturation techniques described above) is likely to give rise to many mutants, most binding to antigen, and a few with higher affinity. To retain all the higher affinity mutants, phages can be incubated with excess biotinylated B7-H3, but with the biotinylated B7-H3 at a concentration of lower molarity than the target molar affinity constant for B7-H3. The high affinity-binding phages can then be captured by streptavidin-coated paramagnetic beads. Such "equilibrium capture" allows the antibodies to be selected according to their affinities of binding, with sensitivity that permits isolation of mutant clones with as little as two-fold higher affinity from a great excess of phages with lower affinity.

Anti-B7-H3 clones may be selected based on performance of activity. In one embodiment, the invention provides anti-B7-H3 antibodies that block the binding between an B7-H3 receptor and its ligand. Anti-B7-H3 antibodies of the invention possessing the properties described herein can be obtained by screening anti-B7-H3 hybridoma clones for the desired properties by any convenient method. For example, if an anti-B7-H3 monoclonal antibody that blocks or does not block the binding of B7-H3 receptor to B7-H3 ligand is desired, the candidate antibody can be tested in a binding competition assay, such as a competitive binding ELISA, wherein plate wells are coated with B7-H3, and a solution of antibody in an excess of B7-H3 receptor is layered onto the coated plates, and bound antibody is detected enzymatically, e.g. contacting the bound antibody with HRP-conjugated anti-Ig antibody or biotinylated anti-Ig antibody and developing the HRP color reaction, e.g. by developing plates with streptavidin-HRP and/or hydrogen peroxide and detecting the HRP color reaction by spectrophotometry at 490 nm with an ELISA plate reader.

3. Isolated Polynucleotides, Vectors, Host Cells and Recombinant Methods

DNA encoding the hybridoma-derived monoclonal antibodies or phage display Fv clones of the invention is readily isolated and sequenced using conventional procedures (e.g. by using oligonucleotide primers designed to specifically amplify the heavy and light chain coding regions of interest from hybridoma or phage DNA template). Once isolated, the DNA can be placed into expression vectors, which are then transfected into host cells such as E. coli cells, simian COS cells, Chinese hamster ovary (CHO) cells, or myeloma cells that do not otherwise produce immunoglobulin protein, to obtain the synthesis of the desired monoclonal antibodies in the recombinant host cells.

DNA encoding the Fv clones of the invention can be combined with known DNA sequences encoding heavy chain and/or light chain constant regions (e.g. the appropriate DNA sequences can be obtained from Kabat et al, supra) to form clones encoding full or partial length heavy and/or light chains. It will be appreciated that constant regions of any isotype can be used for this purpose, including IgG, IgM, IgA, IgD, and IgE constant regions, and that such constant regions can be obtained from any human or animal species. A Fv clone derived from the variable domain DNA of one animal (such as human) species and then fused to constant region DNA of another animal species to form coding sequence(s) for "hybrid", full length heavy chain and/or light chain is included in the definition of "chimeric" and "hybrid" antibody as used herein. In a preferred embodiment, a Fv clone derived from human variable DNA is fused to human constant region DNA to form coding sequence(s) for all human, full or partial length heavy and/or light chains.

DNA encoding anti-B7-H3 antibodies derived from a hybridoma of the invention can also be modified, for example, by substituting the coding sequence for human heavy- and light-chain constant domains in place of homologous murine sequences derived from the hybridoma clone (e.g. as in the method of Morrison et al, Proc. Natl Acad. Sci. USA, 81: 6851-6855 (1984)). DNA encoding a hybridoma or Fv clone-derived antibody or fragment can be further modified by covalently joining to the immunoglobulin coding sequence all or part of the coding sequence for a non-immunoglobulin polypeptide. In this manner, "chimeric" or "hybrid" antibodies are prepared that have the binding specificity of the Fv clone or hybridoma clone-derived antibodies of the invention.

For recombinant production of an antibody of the invention, the nucleic acid encoding it is isolated and inserted into a replicable vector for further cloning (amplification of the DNA) or for expression. DNA encoding the antibody is readily isolated and sequenced using conventional procedures (e.g., by using oligonucleotide probes that are capable of binding specifically to genes encoding the heavy and light chains of the antibody). Many vectors are available. The choice of vector depends in part on the host cell to be used. Generally, preferred host cells are of either prokaryotic or eukaryotic (generally mammalian) origin. It will be appreciated that constant regions of any isotype can be used for this purpose, including IgG, IgM, IgA, IgD, and IgE constant regions, and that such constant regions can be obtained from any human or animal species.

4. Conjugates and Methods for Preparing the Same

Conjugates or immunoconjugate of the anti-B7-H3 antibody or fragment thereof of the present invention and one or more other molecules such as toxins, for example a calicheamicin, maytansinoids, dolastatins, aurostatins, a trichothecene, and CC1065, and the derivatives of these toxins that have toxin activity, are also contemplated herein.

In some embodiments, the conjugate comprises an antibody (full length or fragments) of the invention conjugated to one or more maytansinoid molecules. Maytansinoids are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042).

Immunoconjugates containing maytansinoids, methods of making same, and their therapeutic use are disclosed, for example, in U.S. Pat. Nos. 5,208,020, 5,416,064 and European Patent EP 0 425 235 B1, the disclosures of which are hereby expressly incorporated by reference.

Conjugates of the antibody and maytansinoid may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters.

In some embodiments, the immunoconjugate comprises an antibody of the invention conjugated to dolastatins or dolostatinpeptidic analogs and derivatives, the auristatins (U.S. Pat. Nos. 5,635,483; 5,780,588).

Typically, peptide-based drug moieties can be prepared by forming a peptide bond between two or more amino acids and/or peptide fragments. Such peptide bonds can be prepared, for example, according to the liquid phase synthesis method that is well known in the field of peptide chemistry. The auristatin/dolastatin drug moieties may be prepared according to the methods of: U.S. Pat. Nos. 5,635,483; 5,780,588. See also Doronina (2003) Nat Biotechnol 21(7): 778-784.

The present invention further contemplates an immunoconjugate formed between an antibody and a compound with nucleolytic activity (e.g., a ribonuclease or a DNA endonuclease such as a deoxyribonuclease; DNase).

For selective destruction of the tumor, the antibody may comprise a highly radioactive atom. A variety of radioactive isotopes are available for the production of radioconjugated antibodies. The radio- or other labels may be incorporated in the conjugate in known ways. For example, the peptide may be biosynthesized or may be synthesized by chemical amino acid synthesis using suitable amino acid precursors involving, for example, fluorine-9 in place of hydrogen. "Monoclonal Antibodies in Immunoscintigraphy" (Chatal, CRC Press 1989) describes other methods in detail.

5. Antibody Fragments and Methods for Preparing the Same

The present invention encompasses antibody fragments. In certain circumstances there are advantages of using antibody fragments, rather than whole antibodies. The smaller size of the fragments allows for rapid clearance, and may lead to improved access to solid tumors.

Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992); and Brennan et al., Science, 229:81 (1985)). However, these fragments can now be produced directly by recombinant host cells. Fab, Fv and ScFv antibody fragments can all be expressed in and secreted from *E. coli*, thus allowing the facile production of large amounts of these fragments. Antibody fragments can be isolated from the antibody phage libraries discussed above. Alternatively, Fab'-SH fragments can be directly recovered from *E. coli* and chemically coupled to form F(ab')2 fragments (Carter et al., Bio/Technology 10:163-167 (1992)). According to another approach, F(ab')2 fragments can be isolated directly from recombinant host cell culture. Fab and F(ab')2 fragment with increased in vivo half-life comprising a salvage receptor binding epitope residues are described in U.S. Pat. No. 5,869,046. Other techniques for the production of antibody fragments will be apparent to the skilled practitioner.

In other embodiments, the antibody of choice is a single chain Fv fragment (scFv). See WO 93/16185; U.S. Pat. Nos. 5,571,894; and 5,587,458. Fv and sFv are the only species with intact combining sites that are devoid of constant regions; thus, they are suitable for reduced nonspecific binding during in vivo use. sFv fusion proteins may be constructed to yield fusion of an effector protein at either the amino or the carboxy terminus of an sFv. See Antibody Engineering, ed. Borrebaeck, supra. The antibody fragment may also be a "linear antibody", e.g., as described in U.S. Pat. No. 5,641,870 for example. Such linear antibody fragments may be monospecific or bispecific.

6. Humanized Antibodies and Human Antibodies

The present invention encompasses humanized antibodies. Various methods for humanizing non-human antibodies are known in the art. For example, a humanized antibody can have one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al (1986) Nature 321:522-525; Riechmann et al (1988) Nature 332:323-327; Verhoeyen et al (1988) Science 239:1534-1536), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies. The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework for the humanized antibody (Sims et al (1993) J. Immunol. 151:2296; Chothia et al. (1987) J. Mol. Biol. 196:901. Another method uses a particular framework derived from the consensus sequence of all human antibodies of a particular subgroup of light or heavy chains.

It is further important that antibodies be humanized with retention of high affinity for the antigen and other favorable biological properties. To achieve this goal, according to one method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for B7-H3, is achieved.

Transgenic animals (e.g. mice) that are also capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al, Nature, 362: 255 (1993); Bruggermann et al, Year in Immunol, 7: 33 (1993).

Gene shuffling can also be used to derive human antibodies from non-human, e.g. rodent, antibodies, where the human antibody has similar affinities and specificities to the starting non-human antibody. According to this method, which is also called "epitope imprinting", either the heavy or light chain variable region of a non-human antibody fragment obtained by phage display techniques as described above is replaced with a repertoire of human V domain genes, creating a population of non-human chain/human chain scFv or Fab chimeras. Selection with antigen results in isolation of a non-human chain/human chain chimeric scFv or Fab wherein the human chain restores the antigen binding site destroyed upon removal of the corresponding non-human chain in the primary phage display clone, i.e. the epitope governs (imprints) the choice of the human chain partner. When the process is repeated in order to replace the remaining non-human chain, a human antibody is obtained (see PCT WO 93/06213 published Apr. 1, 1993). Unlike traditional humanization of non-human antibodies by CDR grafting, this technique provides completely human antibodies, which have no FR or CDR residues of non-human origin.

7. Bispecific Antibodies and Methods for Preparing the Same

Bispecific antibodies are monoclonal, preferably human or humanized, antibodies that have binding specificities for at least two different antigens. In the present case, one of the binding specificities is for B7-H3 and the other is for any other antigen. Exemplary bispecific antibodies may bind to two different epitopes of the anti-B7-H3 protein. Bispecific antibodies may also be used to localize cytotoxic agents to cells which express anti-B7-H3. These antibodies possess an B7-H3-binding arm and an arm which binds the cytotoxic agent.

Bispecific antibodies can be prepared as full length antibodies or antibody fragments (e.g. F(ab')2 bispecific antibodies). Methods for making bispecific antibodies are known in the art. Traditionally, the recombinant production of bispecific antibodies is based on the co-expression of two immunoglobulin heavy chain-light chain pairs, where the two heavy chains have different specificities. Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. According to a different and more preferred approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1), containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et ah, Methods in Enzymology, 121:210 (1986).

8. Pharmaceutical Compositions

Therapeutic formulations comprising an antibody of the invention are prepared for storage by mixing the antibody having the desired degree of purity with optional physiologically acceptable carriers, excipients or stabilizers (Remington: The Science and Practice of Pharmacy 20th edition (2000)), in the form of aqueous solutions, lyophilized or other dried formulations. Acceptable carriers, excipients, or stabilizers are nontoxic to recipients at the dosages and concentrations employed, and include buffers such as phosphate, citrate, histidine and other organic acids; antioxidants including ascorbic acid and methionine; preservatives; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes; and/or non-ionic surfactants such as TWEEN™, PLURONICS™ or polyethylene glycol (PEG).

The formulation herein may also contain more than one active compound as necessary for the particular indication being treated, preferably those with complementary activities that do not adversely affect each other. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions.

Sustained-release preparations may be prepared. Suitable examples of sustained-release preparations include semipermeable matrices of solid hydrophobic polymers containing the immunoglobulin of the invention, which matrices are in the form of shaped articles, e.g., films, or microcapsule.

9. Diagnosis and Treatment Uses of Anti-B7-H3 Antibodies

In one aspect, based on specific binding of the antibodies disclosed herein and B7-H3, the antibodies of the present invention can be used in detection and quantitation of a B7-H3 polypeptide in physiological samples, such as urine, plasma, cellular lysate and biopsy samples. Thus, the anti-B7-H3 antibodies disclosed herein can be used diagnostically to monitor B7-H3 levels in tissues, e.g., to determine the progression of cancers and/or the efficacy of a given treatment regimen. A skilled person in the art knows that the B7-H3 antibodies disclosed herein can be coupled with detectable materials to facilitate the detection. In certain embodiments, the anti-B7-H3 antibody or fragment thereof disclosed herein is bound to a solid support to facilitate the detection.

In another aspect, based on specific binding of the antibodies disclosed herein and B7-H3, the antibodies of the present invention can be used in, for example, isolating by affinity chromatography methods or immunoprecipitation methods, analyzing or sorting cells by flow cytometry methods, and detecting a B7-H3 polypeptide within fixed tissue samples or cell smear samples by immunohistochemistry, cytology analysis, ELISA, or immunoprecipitation methods.

In certain embodiments, the B7-H3 molecule to be detected, quantified or analyzed is human B7-H3 protein or fragments thereof. In certain embodiments, the B7-H3 protein or fragment thereof is disposed in a solution, such as a lysis solution or a solution containing a sub-cellular fraction of a fractionated cell, or present on surface of B7-H3-positive cells, or in complexes containing B7-H3 and other cellular components.

The detection method of the present disclosure can be used to detect expression levels of B7-H3 polypeptides in a biological sample in vitro as well as in vivo. In vitro techniques for detection of B7-H3 polypeptides include enzyme linked immunosorbent assays (ELISAs), Western blots, flow cytometry, immunoprecipitations, radioimmunoassay, and immunofluorescence (e.g., IHC). Furthermore, in vivo techniques for detection of B7-H3 polypeptides include introducing into a subject a labeled anti-B7-H3 antibody. By way of example only, the antibody can be labeled with a radioactive marker whose presence and location in a subject can be detected by standard imaging techniques.

Other antibody-based methods useful for detecting protein gene expression include immunoassays, such as the enzyme linked immunosorbent assay (ELISA) and the radio-immunoassay (RIA). Suitable antibody assay labels are known in the art and include enzyme labels, such as, glucose oxidase, and radioisotopes or other radioactive agents and fluorescent labels, such as fluorescein and rhodamine, and biotin.

The B7-H3 antibodies or fragments thereof disclosed herein can be used as diagnostic reagents for any kind of biological sample. In one aspect, the B7-H3 antibodies disclosed herein are useful as diagnostic reagents for human biological samples. B7-H3 antibodies can be used to detect B7-H3 polypeptides in a variety of standard assay formats. Such formats include immunoprecipitation, Western blotting, ELISA, radioimmunoassay, flow cytometry, IHC and immunometric assays.

The present invention also provides for prognostic (or predictive) uses of the anti-B7-H3 antibodies and fragments thereof for determining whether a subject is at risk of developing a medical disease or condition associated with increased B7-H3 polypeptide expression or activity (e.g., detection of a precancerous cell). Thus the anti-B7-H3 antibodies and fragments thereof disclosed herein can be used for prognostic or predictive purpose to prophylactically treat an individual prior to the onset of a medical disease or condition (for example cancer) characterized by or associated with increased B7-H3 polypeptide expression or activity.

Another aspect of the present disclosure provides methods for determining B7-H3 expression in a subject to thereby screen therapeutic or prophylactic compounds for a medical disease or condition (for example cancer) characterized by or associated with increased B7-H3 polypeptide expression or activity.

In certain embodiments, the medical disease or condition characterized by or associated with B7-H3 polypeptide expression or activity or increased B7-H3 polypeptide expression or activity stated above is precancerous condition or cancer. In certain embodiments, the prognostic assays can be utilized to identify a subject having or at risk for developing a cancer. Thus, the present disclosure provides a method for identifying a disease or condition (for example cancer) associated with increased B7-H3 polypeptide expression levels in which a test sample is obtained from a subject and the B7-H3 polypeptide detected, wherein the presence of increased levels of B7-H3 polypeptides compared to a control sample is predictive for a subject having or at risk of developing a disease or condition (for example cancer) associated with increased B7-H3 polypeptide expression levels.

In another aspect, the present disclosure provides methods for determining whether a subject can be effectively treated with a therapeutic agent for a disorder or condition (for example cancer) associated with increased B7-H3 polypeptide expression wherein a biological sample is obtained from the subject and the B7-H3 polypeptide is detected using the B7-H3 antibody. The expression level of the B7-H3 polypeptide in the biological sample obtained from the subject is determined and compared with the B7-H3 expression levels found in a biological sample obtained from a subject who is free of the disease. Elevated levels of the B7-H3 polypeptide in the sample obtained from the subject suspected of having the disease or condition compared with the sample obtained from the healthy subject is indicative of the B7-H3-associated disease or condition (for example cancer) in the subject being tested.

In one aspect, the present disclosure provides for methods of monitoring the treatment efficacy of agents on the expression of B7-H3 polypeptides. Such assays can be applied in drug screening and in clinical trials. For example, the effectiveness of an agent to decrease B7-H3 polypeptide levels can be monitored in clinical trials of subjects exhibiting elevated expression of B7-H3, e.g., patients diagnosed with cancer. An agent that affects the expression of B7-H3 polypeptides can be identified by administering the agent and observing a response. In this way, the expression pattern of the B7-H3 polypeptide can serve as a marker, indicative of the physiological response of the subject to the agent.

The foregoing are merely exemplary assays for using the anti-B7-H3 antibodies and fragments thereof of the present invention. Other methods now or hereafter developed that use the antibodies or fragments thereof for the determination of B7-H3 are included within the scope hereof.

In one aspect, the invention provides methods for treating cancers comprise administering an effective amount of an anti-B7-H3 antibody or fragments thereof specifically binding B7-H3 to a subject in need of such treatment. The antibodies of the present invention can be used to treat, inhibit, delay progression of, prevent/delay recurrence of, ameliorate, or prevent diseases, disorders or conditions associated with expression and/or activity of one or more antigen molecules including B7-H3 molecule, or increased expression and/or activity of one or more antigen molecules including B7-H3 molecule.

For treatment use of the anti-B7-H3 antibody or fragments thereof of the present invention, the appropriate dosage of an antibody of the invention (when used alone or in combination with other agents will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one or multiple times. Depending on the type and severity of the disease, about 1 µg/kg to 15 mg/kg (e.g. 0.1 mg/kg-10 mg/kg) of antibody is a propriate dosage for administration to the patient, whether, for example, by one or more separate administrations, or by continuous infusion.

Antibodies of the invention can be used either alone or in combination with other compositions in a therapy. For instance, an antibody of the present invention may be co-administered with another antibody, steroids (such as inhalable, systemic or cutaneous steroids), chemotherapeutic agent(s) (including cocktails of chemotherapeutic agents, other cytotoxic agent(s), anti-angiogenic agent(s), cytokines, and/or growth inhibitory agent(s). Such combined therapies noted above include combined administration (where the two or more agents are included in the same or separate formulations), and separate administration, in which case, the anti-B7-H3 antibody or fragment thereof of the present invention can be administrated prior to, during and/or following administration of one or more other agents. The effective amounts of therapeutic agents administered in combination depend on such factors as the type of therapeutic agent to be used and the specific patient being treated. and will generally be at the physician's or veterinarian's discretion.

10. Kits and Articles of Manufacture

The present disclosure provides diagnostic methods for determining the expression level of B7-H3. In one particular aspect, the present disclosure provides kits for determining the expression level of B7-H3. The kit comprises an anti-B7-H3 antibody or fragment thereof disclosed herein and instructions about how to use the kit, for example, instructions for collecting samples and/or performing the detection, and/or analyzing the results. The kits are useful for detecting the presence of B7-H3 polypeptides in a biological sample e.g., any body fluid including, but not limited to, e.g., sputum, serum, plasma, lymph, cystic fluid, urine, stool, cerebrospinal fluid, acitic fluid or blood and including biopsy samples of body tissue. The test samples may also be a tumor cell, a normal cell adjacent to a tumor, a normal cell corresponding to the tumor tissue type, a blood cell, a peripheral blood lymphocyte, or combinations thereof.

In certain embodiments, the kit may further comprise one or more other B7-H3 antibodies apart from the anti-B7-H3 antibody of the present invention, which are capable of binding a B7-H3 polypeptide in a biological sample. The one or more of the B7-H3 antibodies may be labeled. In certain embodiments, the kit comprises a first antibody, e.g., attached to a solid support, which binds to a B7-H3 polypeptide; and, optionally; 2) a second, different antibody which binds to either the B7-H3 polypeptide or the first antibody and is conjugated to a detectable label.

The kit can also comprise, e.g., a buffering agent, a preservative or a protein-stabilizing agent. The kit can further comprise components necessary for detecting the detectable-label, e.g., an enzyme or a substrate. The kit can also contain a control sample or a series of control samples, which can be assayed and compared to the test sample. Each component of the kit can be enclosed within an individual container and all of the various containers can be within a single package, along with instructions written on a package insert about how to use the kit, for example, instructions for collecting samples and/or performing the detection, and/or analyzing the results.

In another aspect, an article of manufacture containing materials useful for the treatment, prevention and/or diagnosis of the disorders described above is provided by the present invention. The article of manufacture comprises a container and a label or package insert on or associated with the container with written instructions of, for example, indications to be treated, administration regimens and warnings. Suitable containers include, for example, bottles, vials, syringes, etc. The containers may be formed from a variety of materials such as glass or plastic. The container holds a composition comprising the anti-B7-H3 antibody or fragment thereof of the present invention, which is by itself or when combined with another composition(s) effective for treating, preventing and/or diagnosing the medical disease or condition characterized by or associated with increased expression and/or activity of one or more molecules including B7-H3 polypeptide (e.g., cancers).

The article of manufacture may comprise (a) a first container with a composition contained therein, wherein the composition comprises an antibody of the invention; and (b) a second, third or fourth container with a composition comprising another active ingredient. Additionally, the article of manufacture may further comprise a container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

EXAMPLES

Example 1 Generation of Anti-B7H3 Murine Antibodies

B7H3 KO mice (16-18 g, 6 weeks old, prepared according to the recitations in Suh K W et al, Nat Immunol, 4(9):899-906, 2003, were immunized by subcutaneous injection with human B7H3-Fc fusion protein (R&D system) 10 μg with complete Freund adjuvant (Sigma-Aldrich, Cat #F6881). Immunization was repeated 5 times at an interval of 3 days. 3 days after the final boost, the lymph nodes close to the injection site were carefully dissected out. The lymphocytes were fused with Ag8.653 myeloma cells (Sigma-Aldrich, Cat #85011420) with PEG1500 (Polyethylene Glycol 1500, Roche TM. Cat #:783641, 10×4 ml in 75 mM Hepes, PEG 50% W/V) and cloned with HAT selection (Sigma cat #: H0262) and HFCS (Hybridoma Fusion and Cloning Supplement, 50×, Roche cat #: 11-363-735-001). The hybridoma supernatants were screened for the production of antibodies that can bind to human B7H3-Fc by ELISA and flow cytometry on BAF3 cells transfected with human B7H3 (see Example 2 and 3). The selected murine anti-B7H3 #23 and #27 were humanized using CDR grafting and back mutation.

Antibody humanization by CDR grafting: A selection of acceptor frameworks was made. The variable region sequences of parental antibody were searched in the database of human germline using NCBI Ig-Blast. The CDR sequences of heavy chain and light chain (SEQ ID NOs: 1-12) are shown below respectively. Five diverse human acceptors (i.e. human variable regions with high homology to the parental antibody) for each heavy chain and light chain were chosen. The CDRs of human acceptors were replaced with their mouse counterparts, resulting in the humanized variable region sequences. Five humanized heavy chains and five humanized light chains were designed, synthesized and inserted into an expression vector. The humanized antibodies were expressed, and then used for affinity ranking test. The antibodies with the strongest binding affinity of #23-VH5-VL2, #27-VH2-VL1 and #27-VH2-VL2 were selected for back mutation. Among the variants, the #23-VH5-4/VL2-3, #23-VH5-4/VL2-4, #27-VH2-1/VL2-1, #27-VH2-1/VL2-2, #27-VH2-2/VL2-1 and #27-VH2-2/VL2-2 were selected based on binding and functional assays (SEQ ID Nos: 13-19).

```
#23-CDR1H amino acid sequence
                                        (SEQ ID NO: 1)
GYNENNYWMH

#23-CDR2H amino acid sequence
                                        (SEQ ID NO: 2)
MIHPNSGTFNYNERFKR

#23-CDR3H amino acid sequence
                                        (SEQ ID NO: 3)
STALATDY

#23-CDR1L amino acid sequence
                                        (SEQ ID NO: 4)
SASSSVSYMY

#23-CDR2L amino acid sequence
                                        (SEQ ID NO: 5)
DTSNLAS

#23-CDR3L amino acid sequence
                                        (SEQ ID NO: 6)
QQWSSYPLT

#27-CDR1H amino acid sequence
                                        (SEQ ID NO: 7)
GYTFTNYWMH

#27-CDR2H amino acid sequence
                                        (SEQ ID NO: 8)
MIHPNSGAFNYNERFKT

#27-CDR3H amino acid sequence
                                        (SEQ ID NO: 9)
STALATGY

#27-CDR1L amino acid sequence
                                        (SEQ ID NO: 10)
SASSSVSYMY

#27-CDR2L amino acid sequence
                                        (SEQ ID NO: 11)
DTSNLAS

#27-CDR3L amino acid sequence
                                        (SEQ ID NO: 12)
QQWSSYPLT Variable heavy chain domain (#23-VH5-4) amino
acid sequence
                                        (SEQ ID NO: 13)
QVQLVQSGAEVKKPGESLKISCKASGYNFNNYWMHWVRQRPGKGLEWIG
MIHPNSGTFNYNERFKRKATLTVDKSISTAYLQWSSLKAEDTAMYYCAK
STALATDYWGQGTLVTVSS Variable light chain domain (#23-VL2-3) amino
acid sequence
                                        (SEQ ID NO: 14)
QIVLTQSPSTLSASVGDRVTITCSASSSVSYMYWYQQKPGKAPKLLIYD
TSNLASGVPIRFSGSGSGTSYTLTISSLQPDDFATYYCQQWSSYPLTFG
QGTKLEIK Variable light chain domain (#23-VL2-4) amino
acid sequence
                                        (SEQ ID NO: 15)
QIVLTQSPSTLSASVGDRVTMTCSASSSVSYMYWYQQKPGKAPKLLIYD
TSNLASGVPIRFSGSGSGTSYTLTISSMQPDDFVTYYCQQWSSYPLTFG
QGTKLEIK Variable heavy chain domain (#27-VH2-1) amino
acid sequence
                                        (SEQ ID NO: 16)
QVQLVQSGAEVVKPGASVKVSCKASGYTFTNYWMHWVRQAPGQGLEWMG
MIHPNSGAFNYNERFKTRVTITVDKSTSTAYMELSSLRSEDTAVYYCAR
STALATGYWGQGTLVTVSS
```

-continued
Variable heavy chain domain (#27-VH2-2) amino
acid sequence
                                  (SEQ ID NO: 17)
QVQLVQSGAEVVKPGASVKVSCKASGYTFTNYWMHWVKQAPGQGLEWIG
MIHPNSGAFNYNERFKTRVTITVDKSTSTAYMELSSLRSEDTAVYYCAR
STALATGYWGQGTLLTVSS Variable light chain domain (#27-VL2-1) amino
acid sequence
                                  (SEQ ID NO: 18)
DIQLTQSPSFLSASVGDRVTITCSASSSVSYMYWYQQKPGKSPKLLIYD
TSNLASGVPSRFSGSGSGTEYTLTISSLQPEDFATYYCQQWSSYPLTFG
QGTKLEIK Variable light chain domain (#27-VL2-2) amino
acid sequence
                                  (SEQ ID NO: 19)
DIQLTQSPSFLSASVGDRVTMTCSASSSVSYMYWYQQKPGKSPKLLIYD
TSNLASGVPSRFSGSGSGTEYTLTISSLQPEDFVTYYCQQWSSYPLTFG
QGTKLEIK Example 2. Analysis of Affinity of Humanized Anti-B7H3 Antibodies In order to test humanized anti-B7H3 antibody binding affinity, an ELISA analysis was carried out. Human B7H3, mouse B7H3, and cynomolgus B7H3 (2 ug/ml, in PBS) were coated on MaxiSorp 96-well plates (NUNC, 449824) in 0.5M carbonate/bicarbonate buffer, pH9.6, incubated at 4° C. overnight. Coated plates were blocked with skimmed milk (5%, in PBST) for 1 h. Humanized anti-B7H3 antibodies were diluted and added to the plates, and incubated for 2 h at room temperature. Washed three times with PBST (1×PBS with 0.05% tween-20) to eliminate un-bounded antibodies. Goat anti-Human IgG-HRP (Easybio, BE0122, 1:5000 in PBS) was added and incubated for 1 h. Washed three times with PBST (lx PBS with 0.05% tween-20) to eliminate un-bounded antibodies. TMB (eBioscience, 00-4201-56) was added (50 ul/well) for color rendering and stopped by 2N H2SO4 (50 ul/well). Optical density was measured at 450 nm and 570 nM. As shown in FIG. 1A and Table 1, the antibodies bind to human, mouse and cynomolgus monkey B7H3 protein with high affinity. The binding ability of the mAbs to cynomolgus B7H3 is similar to that for human B7-H3 protein.

TABLE 1

Affinity withhuman, mouse and cynomolgus monkey B7H3 proteins

| | Equilibrium constant, EC50 (nM) | | |
|---|---|---|---|
| | Human B7H3 | Mouse B7H3 | Cynomolgus B7H3 |
| -#27-21(VH2-2-VL2-l) | 0.6177 | 0.5855 | 0.6852 |
| #27-2121 (VH2-1-VL2-1) | 0.5831 | 0.4617 | 0.4944 |
| #27-22 (VH2-2-VL2-2) | 0.3334 | 0.3396 | 0.5842 |
| #23-5423 (VH5-4-VL2-3) | 0.0685 | 1.442 | 0.0420 |
| #23-5424(VH5-4-VL2-4) | 0.1251 | 4.897 | 0.0652 |

In addition, the affinity of the above mAbs was further analyzed by Surface Plasmon Resonance (SPR) binding analysis using Biacore 8K. SPR is the resonant oscillation of conduction electrons at the interface between negative and positive permittivity material stimulated by incident light. Antibodies were immobilized on the sensor chip through Fc capture method. Human B7-H3extracellular domain (NCBI Reference Sequence: NM_025240.2) was used as the analyte. The data of dissociation (kd) and association (ka) rate constants were obtained using Biacore 8K evaluation software. The equilibrium dissociation constants (KD) were calculated from the ratio of kd over ka. As shown in the FIG. 1B and Table 2, all the humanized anti-B7-H3 mAbs bind to human B7-H3 extracellular domain with high affinity (<1.5 nM).

TABLE 2

Kinetic data of selected humanized antibodies

| Ligand | Analyte | $k_a$ (1/Ms) | $k_d$ (1/s) | $K_D$ (M) | Rmax (RU) |
|---|---|---|---|---|---|
| #27-21 | B7-H3 | 2.99E+05 | 4.31E−04 | 1.44E−09 | 15.8 |
| #27-2121 | B7-H3 | 3.06E+05 | 4.33E−04 | 1.42E−09 | 15.4 |
| #27-22 | B7-H3 | 2.88E+05 | 3.65E−04 | 1.26E−09 | 17.6 |
| #23-5423 | B7-H3 | 3.29E+05 | 3.45E−04 | 1.05E−09 | 257.6 |
| #23-5424 | B7-H3 | 2.63E+05 | 3.56E−04 | 1.36E−09 | 225.7 |

Example 3. Humanized Anti-B7H3 Antibodies Binding on B7H3 Stable Cell Line

To evaluate anti-B7H3 antibody binding affinity on cell surface, two stable cell lines of different isoforms of B7H3 (B7H3-2Ig and B7H3-4Ig) were constructed on BaF3 cell line. Full length DNA of human B7H3-2Ig and 4Ig were fully synthetic. The DNA sequences were digested and linked into pcDNA3.4 to construct full length plasmid separately. Electroporation was carried out to transfect full length plasmid into BaF3 cells. Positive clones were screened by G418 (Ameresco, E859-1G, concentration optimized to 1 mg/ml) as well as B7H3 expression tested by flow cytometry.

Cell surface binding affinity was tested with BaF3/B7H3-2Ig and BaF3/B7H3-4Ig the same method separately. Cells were washed with PBS and aliquot to 96-well U-bottom plate with a cell density of 5×10^5 cells/well. For live/dead stain, LIVE/DEAD® Fixable Aqua Dead Cell Stain Kit (Life technologies, L34957) was applied (1:1000 in PBS, 100 ul/well) to cells, and incubated at 4° C. for 10 min FACS buffer (2% FBS in PBS, 100 ul/well) was added to each well to terminate staining. Centrifuge (1200 rpm, 5 min) to discard supernatant and wash with FACS buffer once. Humanized anti-B7H3 antibodies were diluted in FACS buffer to according concentrations and added to each well (100 ul/well). Cells were incubated at 4° C. for 30 min, and then, washed twice with FACS buffer. Alexa Fluor® 594 labeled goat anti-human IgG (Jackson Immuno Research, 109-585-088) was added (1:500 in FACS buffer) to label bounded antibodies. Cells were incubated at 4° C. for 30 min, and then, washed twice with FACS buffer. Cells were analyzed on flow cytometry and results were shown in FIG. 2. The data demonstrate that the antibodies bind to B7H3 expressed on cells with high affinity. For example, the binding EC50 of #27 mAbs is less than 1 nM. The data confirm that the mAbs not only bind to plate-bound human B7-H3 extracellular domain protein, but also potently bind to human B7-H3 molecule expressed on cell surface.

Example 4. Humanized Anti-B7H3 Antibodies Binding Assay on Stimulated PBMC

Peripheral blood mononuclear cells (PBMCs) contain monocytes which under stimulation would up-regulate B7H3 expression on cell surface. This example is to evaluate humanized anti-B7H3 antibody binding affinity on monocytes. Human buffy coat was diluted with PBS to according volume as twice as Ficoll (GE, 17-1440-02). The diluted buffy coat was layered gently on top of Ficoll and centrifuged at 2500 rpm for 40 min at 20° C. without brake. Carefully draw off PBMC slayer in between Ficoll and its transparent supernatant. PBS was added to 5 volumes of PBMCs and centrifuged at 1200 rpm for 10 min at 20° C. Discard supernatant and wash with PBS again. To eliminate platelets, centrifuge at 900 rpm for 8 mM at 20° C. PBMCs were resuspended with culture medium (RPMI-1640 with 10% FBS and 1% PS), counted and aliquot to 96-well plate ($5\times10^5$ cells/well) with LPS added (100 ng/ml). After 24 h incubation, cells were washed with PBS twice. For live/dead stain, LIVE/DEAD® Fixable Aqua Dead Cell Stain Kit (Life technologies, L34957) was applied (1:1000 in PBS, 100 ul/well) to cells, and incubated at 4° C. for 10 min. FACS buffer (2% FBS in PBS, 100 ul/well) was added to each well to terminate staining. Centrifuge (1200 rpm, 5 min) to discard supernatant and wash with FACS buffer once. Humanized anti-B7H3 antibodies were diluted in FACS buffer to according concentrations and added to each well (100 ul/well). Cells were incubated at 4° C. for 30 min, and then, washed twice with FACS buffer. Alexa Fluor® 594 labeled goat anti-human IgG (Jackson Immuno Research, 109-585-088) was added (1:500 in FACS buffer) to label bounded antibodies. Cells were incubated at 4° C. for 30 min, and then, washed twice with FACS buffer. Cells were tested on flow cytometry. Results were shown in FIG. 3. The data show that the antibodies bind to B7H3 expressed on primary cells derived from human PBMCs with high affinity, i.e. the binding EC50 of #27 derived mAbs is less than 1 nM, and the binding EC50 of #23-derived mAbs is less than 3 nM. The data confirm that the humanized mAbs can potently bind to B7-H3 molecule with physiological structure, which is critical for the development of therapeutic antibodies. The mAbs meet the requirements for binding profile of antibody drugs.

Example 5. Humanized Anti-B7H3 Antibody Induced ADCC In Vitro

Humanized anti-B7H3 antibody with IgG1 isotype would mediate antibody-dependent cell-mediated cytotoxicity (ADCC) of effector cells. The stable cell line, BaF3/B7H3-4Ig, was used as target cells while human PBMCs as effector cells. BaF3/B7H3-4Ig cells ($5\times10^7$ cells/ml, in PBS) were labeled with CFSE (Sigma, 21888, 5 nM) at 37° C. in water bath for 10 min avoid light. Complete medium was added at least 5 volumes to cells and quickly incubated on ice for 5 min. Centrifuge to discard supernatant. Resuspend cells with complete medium and aliquot (4000 cells/well, 100 ul/well) to 96-well U-bottom plate. Humanized anti-B7H3 antibodies were diluted to according concentrations and added to labeled cells. The PBMCs effector cells were added to each well in an E:T (Effector cells:Target cells) ratio of 25:1. Cells were incubated at 37° C. in CO2 incubator for 4 h. Cells were washed with PBS once. Dead cells were positively stained with Fixable Viability Dye eFluor™ 660 (eBioscience, 65-0864-18, 1:1000 in PBS). PBMCs effector cells were labeled with anti-CD45 markers (Biolegend, 304032). ADCC percentage equals to the proportion of dead cells in CFSE positive cells. Antibody dependent cell-mediated phagocytosis (ADCP) equals to the proportion of anti-CD45 positive cells in CFSE positive cells. As shown in FIG. 4, humanized anti-B7-H3 antibodies are able to mediate ADCC as well as ADCP in a dose dependent manner. The data suggest that the mAb can be developed as therapeutic drug (depleting antibody drug) to kill the cancer cells. Furthermore, it can be developed to antibody-drug conjugates as it has the ability to bring the chemicals into the target cells, including cancer cells, with highly expressed B7H3 molecule. Those cancers include but not limited to prostate cancer, breast cancer, colon cancer, lung cancer, gastric cancer, renal clear cell carcinoma (Loo K, et al, Clin Cancer Res, 2012).

Example 6. Anti-B7H3 Antibody Blocked B7H3 Inhibition of T Cell Activation

B7H3 is an inhibitor of T cell activation. To investigate the blocking effect of anti-B7H3 antibodies, the PBMCs functional assay was set-up. Anti-CD3 (BD, 555329, 0.125 ug/ml) and B7H3-4Ig (10 ug/ml) in PBS were coated to 96-well plate (100 ul/well) at 4° C. overnight. The plate was washed with PBS once, and blocked with complete medium at 37° C. for 30 min Anti-B7H3 antibodies were diluted in complete medium to according concentrations and added to coated plate. The antibodies were incubated at 37° C. for 1 h and washed with complete medium once. PBMCs were isolated from fresh buffy coat as Example 4 described. After re-suspension in complete medium, PBMCs were aliquot to each well ($3\times10^5$ cells/well, 200 ul/well). Cells were incubated in $CO_2$ incubator overnight. The next day, dead cells were labeled with LIVE/DEAD® Fixable Aqua Dead Cell Stain Kit (Life technologies, L34957). T cells were labeled with anti-CD3 (Biolegend, 317322), anti-CD4 (BD, 562402) and anti-CD8 (BD, 557834), and activation marker CD69 (Biolegend, 310922) was labeled as an indicator of antibody blocking effect. Cells were tested with flow cytometry. As shown in FIG. 5, anti-B7H3 Abs reverse the inhibition effect of B7-H3 on anti-CD3 stimulated T cell activation. Published data have analyzed the role of B7-H3 in murine cancer models (Lee Yh, eta 1, *Cell Research*, 2017), and indicated B7-H3 serves as a critical negative regulator in tumor immunity. The data herein showed the high potential of the mAbs to be developed as therapeutic agents for the treatment of cancers by blocking the B7-H3 bioactivity.

Example 7. Treatment Efficacy of the Anti-B7H3 Antibody

1. B16F10 Murine Melanoma Syngeneic Model in C57BL6/J Mice

The B16F10 tumor cells were maintained in vitro as a monolayer culture in DMEM medium supplemented with 10% fetal bovine serum at 37° C. in an atmosphere of 5% CO2 in air. The tumor cells were routinely subcultured every other day by trypsin-EDTA treatment. Each mouse was inoculated subcutaneously with B16F10 tumor cells ($2\times10^5$) in 0.1 ml of PBS for tumor development. The treatment was started when the mean tumor size reached 129 mm3. Mice were randomized assigned into 4 groups: PBS, anti-B7H3 27-1-5 (PG-DO, 3) or 27-1 (PG-D5, 8, 10) mIgG2b 10 mg/kg, anti-B7H3 23-2-3 mIgG2a 10 mg/kg and 23-2-3 mIgG2b 10 mg/kg, respectively. The treatment schedule in each group was on PG-DO, 3, 5, 8, 10. As shown in FIG. 6, the anti-B7H3 antibody can reduce melanoma tumor growth in in vivo studies. The data demonstrate significant therapeutic effect on B7-H3 expressing cancers including melanoma.

2. SW620 Human Colorectal Adenocarcinoma Xenograft Model in BALB/C Nude Mice

The SW620 tumor cells were maintained in vitro as a monolayer culture in 1640 medium supplemented with 10% fetal bovine serum at 37° C. in an atmosphere of 5% CO2 in air. The tumor cells were routinely subcultured every other day by trypsin-EDTA treatment. Each mouse was inoculated subcutaneously with SW620 tumor cells (5×106) in 0.1 ml of PBS for tumor development. The treatment was started when the mean tumor size reached 188 mm3. Mice were randomized assigned into 2 groups: PBS and anti-B7H3 23-2-3 mIgG2a 10 mg/kg. The treatment schedule in each group was twice/week, 3 weeks continuous. As shown in FIG. 7, the anti-B7H3 antibody can reduce human colorectal adenocarcinoma growth in xenograft model. The data demonstrate significant therapeutic effect on B7-H3 expressing cancers including colorectal adenocarcinoma.

The invention claimed is:

1. An isolated antibody or antigen binding fragment thereof, comprising a heavy chain (HC) variable region sequence and a light chain (LC) variable region sequence, wherein the antibody binds to an extracellular domain of B7-H3 with a binding affinity of about 1.5 nM or better than 1.5 nM as determined by SPR analysis
wherein the HC comprises
(a) a HC CDR1 comprising the amino acid sequence GYNFNNYWMH (SEQ ID NO: 1); and
(b) a HC CDR2 comprising the amino acid sequence MIHPNSGTFNYNERFKR (SEQ ID NO: 2); and
(c) a HC CDR3 comprising the amino acid sequence STALATDY (SEQ ID NO: 3); and wherein
the LC comprises
(a) a LC CDR1 comprising the amino acid sequence SASSSVSYMY (SEQ ID NO: 4); and
(b) a LC CDR2 comprising the amino acid sequence DTSNLAS (SEQ ID NO: 5); and
(c) a LC CDR3 comprising the amino acid sequence QQWSSYPLT (SEQ ID NO: 6);
or wherein the HC comprises
(a) a HC CDR1 comprising the amino acid sequence GYTFTNYWMH (SEQ ID NO: 7); and
(b) a HC CDR2 comprising the amino acid sequence MIHPNSGAFNYNERFKT (SEQ ID NO: 8); and
(c) a HC CDR3 comprising the amino acid sequence STALATGY (SEQ ID NO: 9); and the LC comprises
(a) a LC CDR1 comprising the amino acid sequence SASSSVSYMY (SEQ ID NO: 10); and
(b) a LC CDR2 comprising the amino acid sequence DTSNLAS (SEQ ID NO: 11); and
(c) a LC CDR3 comprising the amino acid sequence QQWSSYPLT (SEQ ID NO: 12).

2. The antibody or antigen binding fragment of claim 1 wherein the antibody is a chimeric antibody, humanized antibody, or murine antibody.

3. The antibody or antigen binding fragment of claim 1, wherein the HC variable region sequence comprises the amino acid sequence selected from the group consisting of SEQ ID NO: 13, SEQ ID NO: 16, SEQ ID NO: 17, and an amino acid sequence having more than 80%, 85%, 90%, 91%, 92%, 93%, 94%, 95%, 96%, 97%, 98% or 99% identity with any one of SEQ ID NOS: 13, 16 and 17.

4. The antibody or antigen binding fragment of claim 1 wherein the LC variable region sequence comprises the amino acid sequence selected from the group consisting of SEQ ID NO: 14, SEQ ID NO: 15, SEQ ID NO: 18, SEQ ID NO: 19, and an amino acid sequence having more than 80%, 85%, 90%, 91%, 92%, 93%, 94%, 95%, 96%, 97%, 98% or 99% identity with any one of SEQ ID NOS: 14, 15, 18 and 19.

5. The antibody or antigen binding fragment of claim 1 wherein the HC variable region sequence comprises the amino acid sequence of SEQ ID NO: 13 and the LC variable region sequence comprises the amino acid sequence of SEQ ID NO: 14 or SEQ ID NO: 15.

6. The antibody or antigen binding fragment of claim 1 wherein the HC variable region sequence comprises the amino acid sequence of SEQ ID NO: 16 or SEQ ID NO: 17 and the LC variable region sequence comprises the amino acid sequence of SEQ ID NO: 18 or SEQ ID NO: 19.

7. The antibody or antigen binding fragment of claim 1 wherein the antibody is an IgG1, lgG2 or lgG4 isotype.

8. A bispecific molecule comprising the antibody or antigen binding fragment of claim 1 and a second antibody or antigen binding fragment thereof.

9. A bispecific molecule of claim 8, wherein the second antibody or antigen binding fragment thereof specifically binds to a tumor antigen expressed on the surface of a tumor cell, wherein the tumor antigen is selected from the group consisting of A33; ADAM-9; ALCAM; BAGE; beta-catenin; CA125; Carboxypeptidase M; CD103; CD19; CD20; CD22; CD23; CD25; CD27; CD28; CD36; CD40/CD154; CD45; CD46; CD5; CD56; CD79a/CD79b; CDK4; CEA; CTLA4; Cytokeratin 8; EGF-R; EphA2; ErbB1; ErbB3; ErbB4; GAGE-1; GAGE-2; GD2/GD3/GM2; HER-2/neu; human papillomavirus-E6; human papillomavirus-E7; JAM-3; KID3; KID31; KSA (17-1A); LUCA-2; MAGE-1; MAGE-3; MART; MUC-1; MUM-1; N-acetyl-glucosaminyltransferase; Oncostatin M; p15; PIPA; PSA; PSMA; ROR1; TNF-β receptor; TNF-α receptor; TNF-γ receptor; Transferrin Receptor; and VEGF receptor.

10. A polypeptide comprising the antibody or antigen binding fragment of claim 1 or comprising the HC variable region and/or LC variable region of the antibody or antigen binding fragment thereof of claim 1.

11. An immunoconjugate comprising the antibody or antigen binding fragment of claim 1 linked to a therapeutic agent.

12. The immunoconjugate of claim 11, wherein the therapeutic agent is a cytotoxin or a radioactive isotope.

13. A composition comprising the antibody or antigen binding fragment of claim 1,
and a pharmaceutically acceptable carrier.

14. The composition of claim 13, further comprising an anti-cancer agent, wherein the agent is an antibody, a chemotherapeutic agent, a radiation therapeutic agent, a hormonal therapeutic agent, a toxin or an immunotherapeutic agent.

15. An isolated nucleic acid encoding the HC variable region and/or LC variable region of the antibody or antigen binding fragment of claim 1.

16. The antibody or antigen binding fragment thereof of claim 1, wherein the antibody further comprises a human acceptor framework.

17. The antibody or antigen binding fragment thereof of claim 1, wherein the antigen binding fragment is selected from the group consisting of Fab, F(ab')$_2$, Fab', scFv, and Fv.

* * * * *

SEQUENCE LISTING

```
<160> NUMBER OF SEQ ID NOS: 19

<210> SEQ ID NO 1
<211> LENGTH: 10
<212> TYPE: PRT
<213> ORGANISM: Artificial Sequence
<220> FEATURE:
<223> OTHER INFORMATION: #23-CDR1H amino acid sequence

<400> SEQUENCE: 1

Gly Tyr Asn Phe Asn Asn Tyr Trp Met His
1               5                   10

<210> SEQ ID NO 2
<211> LENGTH: 17
<212> TYPE: PRT
<213> ORGANISM: Artificial Sequence
<220> FEATURE:
<223> OTHER INFORMATION: #23-CDR2H amino acid sequence

<400> SEQUENCE: 2

Met Ile His Pro Asn Ser Gly Thr Phe Asn Tyr Asn Glu Arg Phe Lys
1               5                   10                  15

Arg

<210> SEQ ID NO 3
<211> LENGTH: 8
<212> TYPE: PRT
<213> ORGANISM: Artificial Sequence
<220> FEATURE:
<223> OTHER INFORMATION: #23-CDR3H amino acid sequence

<400> SEQUENCE: 3

Ser Thr Ala Leu Ala Thr Asp Tyr
1               5

<210> SEQ ID NO 4
<211> LENGTH: 10
<212> TYPE: PRT
<213> ORGANISM: Artificial Sequence
<220> FEATURE:
<223> OTHER INFORMATION: #23-CDR1L amino acid sequence

<400> SEQUENCE: 4

Ser Ala Ser Ser Ser Val Ser Tyr Met Tyr
1               5                   10

<210> SEQ ID NO 5
<211> LENGTH: 7
<212> TYPE: PRT
<213> ORGANISM: Artificial Sequence
<220> FEATURE:
<223> OTHER INFORMATION: #23-CDR2L amino acid sequence
```

```
<400> SEQUENCE: 5

Asp Thr Ser Asn Leu Ala Ser
1               5

<210> SEQ ID NO 6
<211> LENGTH: 9
<212> TYPE: PRT
<213> ORGANISM: Artificial Sequence
<220> FEATURE:
<223> OTHER INFORMATION: #23-CDR3L amino acid sequence

<400> SEQUENCE: 6

Gln Gln Trp Ser Ser Tyr Pro Leu Thr
1               5

<210> SEQ ID NO 7
<211> LENGTH: 10
<212> TYPE: PRT
<213> ORGANISM: Artificial Sequence
<220> FEATURE:
<223> OTHER INFORMATION: #27-CDR1H amino acid sequence

<400> SEQUENCE: 7

Gly Tyr Thr Phe Thr Asn Tyr Trp Met His
1               5                   10

<210> SEQ ID NO 8
<211> LENGTH: 17
<212> TYPE: PRT
<213> ORGANISM: Artificial Sequence
<220> FEATURE:
<223> OTHER INFORMATION: #27-CDR2H amino acid sequence

<400> SEQUENCE: 8

Met Ile His Pro Asn Ser Gly Ala Phe Asn Tyr Asn Glu Arg Phe Lys
1               5                   10                  15

Thr

<210> SEQ ID NO 9
<211> LENGTH: 8
<212> TYPE: PRT
<213> ORGANISM: Artificial Sequence
<220> FEATURE:
<223> OTHER INFORMATION: #27-CDR3H amino acid sequence

<400> SEQUENCE: 9

Ser Thr Ala Leu Ala Thr Gly Tyr
1               5

<210> SEQ ID NO 10
<211> LENGTH: 10
<212> TYPE: PRT
<213> ORGANISM: Artificial Sequence
<220> FEATURE:
<223> OTHER INFORMATION: #27-CDR1L amino acid sequence

<400> SEQUENCE: 10

Ser Ala Ser Ser Ser Val Ser Tyr Met Tyr
1               5                   10

<210> SEQ ID NO 11
<211> LENGTH: 7
<212> TYPE: PRT
<213> ORGANISM: Artificial Sequence
<220> FEATURE:
```

<223> OTHER INFORMATION: #27-CDR2L amino acid sequence

<400> SEQUENCE: 11

Asp Thr Ser Asn Leu Ala Ser
1               5

<210> SEQ ID NO 12
<211> LENGTH: 9
<212> TYPE: PRT
<213> ORGANISM: Artificial Sequence
<220> FEATURE:
<223> OTHER INFORMATION: #27-CDR3L amino acid sequence

<400> SEQUENCE: 12

Gln Gln Trp Ser Ser Tyr Pro Leu Thr
1               5

<210> SEQ ID NO 13
<211> LENGTH: 117
<212> TYPE: PRT
<213> ORGANISM: Artificial Sequence
<220> FEATURE:
<223> OTHER INFORMATION: Variable heavy chain domain (#23-VH5-4) amino
      acid sequence

<400> SEQUENCE: 13

Gln Val Gln Leu Val Gln Ser Gly Ala Glu Val Lys Lys Pro Gly Glu
1               5                   10                  15

Ser Leu Lys Ile Ser Cys Lys Ala Ser Gly Tyr Asn Phe Asn Asn Tyr
                20                  25                  30

Trp Met His Trp Val Arg Gln Arg Pro Gly Lys Gly Leu Glu Trp Ile
            35                  40                  45

Gly Met Ile His Pro Asn Ser Gly Thr Phe Asn Tyr Asn Glu Arg Phe
        50                  55                  60

Lys Arg Lys Ala Thr Leu Thr Val Asp Lys Ser Ile Ser Thr Ala Tyr
65                  70                  75                  80

Leu Gln Trp Ser Ser Leu Lys Ala Glu Asp Thr Ala Met Tyr Tyr Cys
                85                  90                  95

Ala Lys Ser Thr Ala Leu Ala Thr Asp Tyr Trp Gly Gln Gly Thr Leu
            100                 105                 110

Val Thr Val Ser Ser
        115

<210> SEQ ID NO 14
<211> LENGTH: 106
<212> TYPE: PRT
<213> ORGANISM: Artificial Sequence
<220> FEATURE:
<223> OTHER INFORMATION: Variable light chain domain (#23-VL2-3) amino
      acid sequence

<400> SEQUENCE: 14

Gln Ile Val Leu Thr Gln Ser Pro Ser Thr Leu Ser Ala Ser Val Gly
1               5                   10                  15

Asp Arg Val Thr Ile Thr Cys Ser Ala Ser Ser Ser Val Ser Tyr Met
                20                  25                  30

Tyr Trp Tyr Gln Gln Lys Pro Gly Lys Ala Pro Lys Leu Leu Ile Tyr
            35                  40                  45

Asp Thr Ser Asn Leu Ala Ser Gly Val Pro Ile Arg Phe Ser Gly Ser
        50                  55                  60

Gly Ser Gly Thr Ser Tyr Thr Leu Thr Ile Ser Ser Leu Gln Pro Asp

```
                65                  70                  75                  80
Asp Phe Ala Thr Tyr Tyr Cys Gln Gln Trp Ser Ser Tyr Pro Leu Thr
                    85                  90                  95

Phe Gly Gln Gly Thr Lys Leu Glu Ile Lys
                100                 105

<210> SEQ ID NO 15
<211> LENGTH: 106
<212> TYPE: PRT
<213> ORGANISM: Artificial Sequence
<220> FEATURE:
<223> OTHER INFORMATION: Variable light chain domain (#23-VL2-4) amino
      acid sequence

<400> SEQUENCE: 15

Gln Ile Val Leu Thr Gln Ser Pro Ser Thr Leu Ser Ala Ser Val Gly
1               5                   10                  15

Asp Arg Val Thr Met Thr Cys Ser Ala Ser Ser Ser Val Ser Tyr Met
                20                  25                  30

Tyr Trp Tyr Gln Gln Lys Pro Gly Lys Ala Pro Lys Leu Leu Ile Tyr
                35                  40                  45

Asp Thr Ser Asn Leu Ala Ser Gly Val Pro Ile Arg Phe Ser Gly Ser
            50                  55                  60

Gly Ser Gly Thr Ser Tyr Thr Leu Thr Ile Ser Ser Met Gln Pro Asp
65                  70                  75                  80

Asp Phe Val Thr Tyr Tyr Cys Gln Gln Trp Ser Ser Tyr Pro Leu Thr
                    85                  90                  95

Phe Gly Gln Gly Thr Lys Leu Glu Ile Lys
                100                 105

<210> SEQ ID NO 16
<211> LENGTH: 117
<212> TYPE: PRT
<213> ORGANISM: Artificial Sequence
<220> FEATURE:
<223> OTHER INFORMATION: Variable heavy chain domain (#27-VH2-1) amino
      acid sequence

<400> SEQUENCE: 16

Gln Val Gln Leu Val Gln Ser Gly Ala Glu Val Val Lys Pro Gly Ala
1               5                   10                  15

Ser Val Lys Val Ser Cys Lys Ala Ser Gly Tyr Thr Phe Thr Asn Tyr
                20                  25                  30

Trp Met His Trp Val Arg Gln Ala Pro Gly Gln Gly Leu Glu Trp Met
                35                  40                  45

Gly Met Ile His Pro Asn Ser Gly Ala Phe Asn Tyr Asn Glu Arg Phe
            50                  55                  60

Lys Thr Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                    85                  90                  95

Ala Arg Ser Thr Ala Leu Ala Thr Gly Tyr Trp Gly Gln Gly Thr Leu
                100                 105                 110

Val Thr Val Ser Ser
            115

<210> SEQ ID NO 17
<211> LENGTH: 117
<212> TYPE: PRT
```

```
<213> ORGANISM: Artificial Sequence
<220> FEATURE:
<223> OTHER INFORMATION: Variable heavy chain domain (#27-VH2-2) amino
      acid sequence

<400> SEQUENCE: 17

Gln Val Gln Leu Val Gln Ser Gly Ala Glu Val Val Lys Pro Gly Ala
1               5                   10                  15

Ser Val Lys Val Ser Cys Lys Ala Ser Gly Tyr Thr Phe Thr Asn Tyr
            20                  25                  30

Trp Met His Trp Val Lys Gln Ala Pro Gly Gln Gly Leu Glu Trp Ile
        35                  40                  45

Gly Met Ile His Pro Asn Ser Gly Ala Phe Asn Tyr Asn Glu Arg Phe
    50                  55                  60

Lys Thr Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Thr Ala Leu Ala Thr Gly Tyr Trp Gly Gln Gly Thr Leu
            100                 105                 110

Leu Thr Val Ser Ser
        115

<210> SEQ ID NO 18
<211> LENGTH: 106
<212> TYPE: PRT
<213> ORGANISM: Artificial Sequence
<220> FEATURE:
<223> OTHER INFORMATION: Variable light chain domain (#27-VL2-1) amino
      acid sequence

<400> SEQUENCE: 18

Asp Ile Gln Leu Thr Gln Ser Pro Ser Phe Leu Ser Ala Ser Val Gly
1               5                   10                  15

Asp Arg Val Thr Ile Thr Cys Ser Ala Ser Ser Ser Val Ser Tyr Met
            20                  25                  30

Tyr Trp Tyr Gln Gln Lys Pro Gly Lys Ser Pro Lys Leu Leu Ile Tyr
        35                  40                  45

Asp Thr Ser Asn Leu Ala Ser Gly Val Pro Ser Arg Phe Ser Gly Ser
    50                  55                  60

Gly Ser Gly Thr Glu Tyr Thr Leu Thr Ile Ser Ser Leu Gln Pro Glu
65                  70                  75                  80

Asp Phe Ala Thr Tyr Tyr Cys Gln Gln Trp Ser Ser Tyr Pro Leu Thr
                85                  90                  95

Phe Gly Gln Gly Thr Lys Leu Glu Ile Lys
            100                 105

<210> SEQ ID NO 19
<211> LENGTH: 106
<212> TYPE: PRT
<213> ORGANISM: Artificial Sequence
<220> FEATURE:
<223> OTHER INFORMATION: Variable light chain domain (#27-VL2-2) amino
      acid sequence

<400> SEQUENCE: 19

Asp Ile Gln Leu Thr Gln Ser Pro Ser Phe Leu Ser Ala Ser Val Gly
1               5                   10                  15

Asp Arg Val Thr Met Thr Cys Ser Ala Ser Ser Ser Val Ser Tyr Met
            20                  25                  30
```

```
Tyr Trp Tyr Gln Gln Lys Pro Gly Lys Ser Pro Lys Leu Leu Ile Tyr
        35                  40                  45

Asp Thr Ser Asn Leu Ala Ser Gly Val Pro Ser Arg Phe Ser Gly Ser
    50                  55                  60

Gly Ser Gly Thr Glu Tyr Thr Leu Thr Ile Ser Ser Leu Gln Pro Glu
65              70                  75                  80

Asp Phe Val Thr Tyr Tyr Cys Gln Gln Trp Ser Ser Tyr Pro Leu Thr
                85                  90                  95

Phe Gly Gln Gly Thr Lys Leu Glu Ile Lys
            100                 105
```